(12) United States Patent
Bradley

(10) Patent No.: US 11,318,310 B1
(45) Date of Patent: May 3, 2022

(54) NEUROMODULATION FOR ALTERING AUTONOMIC FUNCTIONS, AND ASSOCIATED SYSTEMS AND METHODS

(71) Applicant: Nevro Corp., Redwood City, CA (US)

(72) Inventor: Kerry Bradley, Glendale, CA (US)

(73) Assignee: Nevro Corp., Redwood City, CA (US)

(*) Notice: Subject to any disclaimer, the term of this patent is extended or adjusted under 35 U.S.C. 154(b) by 0 days.

(21) Appl. No.: 15/333,763

(22) Filed: Oct. 25, 2016

Related U.S. Application Data

(60) Provisional application No. 62/385,073, filed on Sep. 8, 2016, provisional application No. 62/246,514, filed on Oct. 26, 2015.

(51) Int. Cl.
*A61N 1/36* (2006.01)
*A61N 1/05* (2006.01)

(52) U.S. Cl.
CPC ........ *A61N 1/36114* (2013.01); *A61N 1/0551* (2013.01); *A61N 1/3606* (2013.01); *A61N 1/36007* (2013.01); *A61N 1/36117* (2013.01); *A61N 1/36135* (2013.01); *A61N 1/36171* (2013.01); *A61N 1/36175* (2013.01)

(58) Field of Classification Search
CPC .............. A61N 1/36114; A61N 1/3606; A61N 1/36117; A61N 1/36135; A61N 1/36171; A61N 1/0551; A61N 1/36007; A61N 1/36175
USPC .......................................................... 607/40
See application file for complete search history.

(56) References Cited

U.S. PATENT DOCUMENTS

| | | | |
|---|---|---|---|
| 1,597,061 A | 8/1926 | Cultra |
| 2,622,601 A | 12/1952 | Nemec |
| 3,195,540 A | 7/1965 | Waller |
| 3,279,468 A | 10/1966 | Vine |
| 3,449,768 A | 6/1969 | Doyle |
| 3,646,940 A | 3/1972 | Timm et al. |
| 3,724,467 A | 4/1973 | Avery et al. |
| 3,727,616 A | 4/1973 | Lenzkes |
| 3,817,254 A | 6/1974 | Maurer |
| 3,822,708 A | 7/1974 | Zilber |

(Continued)

FOREIGN PATENT DOCUMENTS

| | | |
|---|---|---|
| CN | 101175530 | 5/2008 |
| DE | 10318071 A1 | 11/2004 |

(Continued)

OTHER PUBLICATIONS

"The Need for Mechanism-Based Medicine in Neuromodulation," Neuromodulation: Technology at the Neural Interface, 2012, 7 pages.

(Continued)

*Primary Examiner* — Mallika D Fairchild
*Assistant Examiner* — Minh Duc G Pham
(74) *Attorney, Agent, or Firm* — Perkins Coie LLP

(57) ABSTRACT

Electrical stimulation, including high frequency stimulation, for altering autonomic functions, and associated systems and methods are disclosed. A representative method includes directing an electrical signal to a target tissue at (a) a ventral region of the patient's spinal canal, (b) a sympathetic chain structure, or (c) both (a) and (b), at a frequency in a range from 1 kHz to 100 kHz, and an amplitude that does not generate an objectionable, patient-detectable sensation.

36 Claims, 10 Drawing Sheets

(56) References Cited

U.S. PATENT DOCUMENTS

| | | |
|---|---|---|
| 3,893,463 A | 7/1975 | Williams |
| 4,014,347 A | 3/1977 | Halleck et al. |
| 4,023,574 A | 5/1977 | Nemec |
| 4,055,190 A | 10/1977 | Tany et al. |
| 4,096,866 A | 6/1978 | Fischell |
| 4,148,321 A | 4/1979 | Wyss et al. |
| 4,155,366 A | 5/1979 | Di Mucci |
| 4,289,136 A | 9/1981 | Rienzo, Sr. |
| 4,315,503 A | 2/1982 | Ryaby et al. |
| 4,379,462 A | 4/1983 | Borkan et al. |
| 4,414,986 A | 11/1983 | Dickhudt et al. |
| 4,459,989 A | 7/1984 | Borkan |
| 4,535,777 A | 8/1985 | Castel |
| 4,541,432 A | 9/1985 | Molina-Negro et al. |
| 4,550,733 A | 11/1985 | Liss et al. |
| 4,607,639 A | 8/1986 | Tanagho |
| 4,608,985 A | 9/1986 | Crish et al. |
| 4,612,934 A | 9/1986 | Borkan et al. |
| 4,649,935 A | 3/1987 | Charmillot et al. |
| 4,702,254 A | 10/1987 | Zabara |
| 4,735,204 A | 4/1988 | Sussman et al. |
| 4,739,764 A | 4/1988 | Lue et al. |
| 4,764,132 A | 8/1988 | Stutz, Jr. |
| 4,784,142 A | 11/1988 | Liss et al. |
| 4,793,353 A | 12/1988 | Borkan et al. |
| 4,841,973 A | 6/1989 | Stecker |
| RE33,420 E | 11/1990 | Sussman et al. |
| 4,989,605 A | 2/1991 | Rossen |
| 5,002,053 A | 3/1991 | Garcia-Rill |
| 5,188,104 A | 2/1993 | Wernicke et al. |
| 5,284,153 A | 2/1994 | Raymond et al. |
| 5,306,291 A | 4/1994 | Kroll et al. |
| 5,330,515 A | 7/1994 | Rutecki et al. |
| 5,335,657 A | 8/1994 | Terry, Jr. et al. |
| 5,354,320 A | 10/1994 | Schaldach et al. |
| 5,417,719 A | 5/1995 | Hull |
| 5,501,703 A | 3/1996 | Holsheimer et al. |
| 5,514,175 A | 5/1996 | Kim et al. |
| 5,531,774 A | 7/1996 | Schulman et al. |
| 5,540,730 A | 7/1996 | Terry, Jr. et al. |
| 5,540,734 A | 7/1996 | Zabara |
| 5,562,717 A | 10/1996 | Tippey |
| 5,573,552 A | 11/1996 | Hansjurgens et al. |
| 5,643,330 A | 7/1997 | Holsheimer et al. |
| 5,702,428 A | 12/1997 | Tippey et al. |
| 5,707,396 A | 1/1998 | Benabid |
| 5,716,377 A | 2/1998 | Rise |
| 5,755,758 A | 5/1998 | Wolozko |
| 5,776,170 A | 7/1998 | MacDonald et al. |
| 5,792,187 A | 8/1998 | Adams |
| 5,830,151 A | 11/1998 | Hadzic et al. |
| 5,833,709 A | 11/1998 | Rise |
| 5,853,373 A | 12/1998 | Griffith et al. |
| 5,893,883 A | 4/1999 | Torgerson |
| 5,895,416 A | 4/1999 | Barreras |
| 5,925,070 A | 7/1999 | King |
| 5,938,690 A | 8/1999 | Law |
| 5,948,007 A | 9/1999 | Starkebaum et al. |
| 5,976,110 A | 11/1999 | Greengrass et al. |
| 5,983,141 A | 11/1999 | Sluijter et al. |
| 5,995,872 A | 11/1999 | Bourgeois |
| 6,002,964 A | 12/1999 | Feler et al. |
| 6,014,588 A | 1/2000 | Fitz |
| 6,027,456 A | 2/2000 | Feler et al. |
| 6,049,701 A | 4/2000 | Sparksman |
| 6,104,957 A | 8/2000 | Alo et al. |
| 6,159,163 A | 12/2000 | Strauss et al. |
| 6,161,044 A | 12/2000 | Silverstone |
| 6,161,048 A | 12/2000 | Sluijter et al. |
| 6,167,305 A | 12/2000 | Cammilli et al. |
| 6,167,311 A | 12/2000 | Rezai |
| 6,176,242 B1 | 1/2001 | Rise |
| 6,233,488 B1 | 5/2001 | Hess |
| 6,238,423 B1 | 5/2001 | Bardy |
| 6,246,912 B1 | 6/2001 | Sluijter et al. |
| 6,259,952 B1 | 7/2001 | Sluijter et al. |
| 6,314,325 B1 | 11/2001 | Fitz |
| 6,319,241 B1 | 11/2001 | King et al. |
| 6,341,236 B1 | 1/2002 | Osorio et al. |
| 6,356,786 B1 | 3/2002 | Rezai et al. |
| 6,366,814 B1 | 4/2002 | Boveja |
| 6,381,496 B1 | 4/2002 | Meadows et al. |
| 6,393,325 B1 | 5/2002 | Mann et al. |
| 6,397,108 B1 | 5/2002 | Camps et al. |
| 6,405,079 B1 | 6/2002 | Ansarinia |
| 6,421,566 B1 | 7/2002 | Holsheimer |
| 6,440,090 B1 | 8/2002 | Schallhorn |
| 6,473,644 B1 | 10/2002 | Terry, Jr. et al. |
| 6,487,446 B1 | 11/2002 | Hill et al. |
| 6,505,074 B2 | 1/2003 | Boveja et al. |
| 6,505,078 B1 | 1/2003 | King et al. |
| 6,510,347 B2 | 1/2003 | Borkan |
| 6,516,227 B1 | 2/2003 | Meadows et al. |
| 6,526,318 B1 | 2/2003 | Ansarinia |
| 6,571,127 B1 | 5/2003 | Ben-Haim et al. |
| 6,584,358 B2 | 6/2003 | Carter et al. |
| 6,587,724 B2 | 7/2003 | Mann |
| 6,587,727 B2 | 7/2003 | Osorio et al. |
| 6,600,954 B2 | 7/2003 | Cohen et al. |
| 6,609,030 B1 | 8/2003 | Rezai et al. |
| 6,609,031 B1 | 8/2003 | Law et al. |
| 6,610,713 B2 | 8/2003 | Tracey |
| 6,622,047 B2 | 9/2003 | Barrett et al. |
| 6,622,048 B1 | 9/2003 | Mann |
| 6,659,968 B1 | 12/2003 | McClure |
| 6,662,051 B1 | 12/2003 | Eraker et al. |
| 6,671,556 B2 | 12/2003 | Osorio et al. |
| 6,671,557 B1 | 12/2003 | Gliner |
| 6,675,046 B2 | 1/2004 | Holsheimer |
| 6,684,105 B2 | 1/2004 | Cohen et al. |
| 6,687,538 B1 | 2/2004 | Hrdlicka et al. |
| 6,701,190 B2 | 3/2004 | Gliner |
| 6,712,753 B2 | 3/2004 | Manne |
| 6,714,822 B2 | 3/2004 | King et al. |
| 6,721,603 B2 | 4/2004 | Zabara et al. |
| 6,795,737 B2 | 9/2004 | Gielen et al. |
| 6,836,685 B1 | 12/2004 | Fitz |
| 6,856,315 B2 | 2/2005 | Eberlein |
| 6,871,090 B1 | 3/2005 | He et al. |
| 6,871,099 B1 | 3/2005 | Whitehurst et al. |
| 6,885,888 B2 | 4/2005 | Rezai |
| 6,892,097 B2 | 5/2005 | Holsheimer et al. |
| 6,895,280 B2 | 5/2005 | Meadows et al. |
| 6,907,293 B2 | 6/2005 | Grill et al. |
| 6,907,295 B2 | 6/2005 | Gross et al. |
| 6,920,357 B2 | 7/2005 | Osorio et al. |
| 6,923,784 B2 | 8/2005 | Stein |
| 6,928,320 B2 | 8/2005 | King |
| 6,941,173 B2 | 9/2005 | Nachum |
| 6,950,707 B2 | 9/2005 | Whitehurst |
| 6,961,618 B2 | 11/2005 | Osorio et al. |
| 6,968,237 B2 | 11/2005 | Doan et al. |
| 6,973,346 B2 | 12/2005 | Hafer et al. |
| 6,988,006 B2 | 1/2006 | King et al. |
| 6,990,376 B2 | 1/2006 | Tanagho et al. |
| 7,024,246 B2 | 4/2006 | Acosta et al. |
| 7,024,247 B2 | 4/2006 | Gliner et al. |
| 7,047,079 B2 | 5/2006 | Erickson |
| 7,047,084 B2 | 5/2006 | Erickson et al. |
| 7,054,686 B2 | 5/2006 | MacDonald |
| 7,076,307 B2 | 7/2006 | Boveja et al. |
| 7,082,333 B1 | 7/2006 | Bauhahn et al. |
| 7,117,034 B2 | 10/2006 | Kronberg |
| 7,127,297 B2 | 10/2006 | Law et al. |
| 7,146,224 B2 | 12/2006 | King |
| 7,149,574 B2 | 12/2006 | Yun et al. |
| 7,158,826 B1 | 1/2007 | Kroll et al. |
| 7,162,303 B2 | 1/2007 | Levin et al. |
| 7,162,304 B1 | 1/2007 | Bradley |
| 7,167,750 B2 | 1/2007 | Knudson et al. |
| 7,174,215 B2 | 2/2007 | Bradley |
| 7,177,690 B2 | 2/2007 | Woods et al. |
| 7,177,702 B2 | 2/2007 | Wallace et al. |
| 7,180,760 B2 | 2/2007 | Varrichio et al. |

(56) References Cited

U.S. PATENT DOCUMENTS

| | | |
|---|---|---|
| 7,206,640 B1 | 4/2007 | Overstreet |
| 7,212,865 B2 | 5/2007 | Cory |
| 7,225,035 B2 | 5/2007 | Brabec et al. |
| 7,228,179 B2 | 6/2007 | Campen et al. |
| 7,231,254 B2 | 6/2007 | DiLorenzo |
| 7,236,822 B2 | 6/2007 | Dobak, III |
| 7,236,830 B2 | 6/2007 | Gliner |
| 7,239,912 B2 | 7/2007 | Dobak, III |
| 7,242,984 B2 | 7/2007 | DiLorenzo |
| 7,251,529 B2 | 7/2007 | Greenwood-Van Meerveld |
| 7,252,090 B2 | 8/2007 | Goetz |
| 7,254,445 B2 | 8/2007 | Law et al. |
| 7,260,436 B2 | 8/2007 | Kilgore et al. |
| 7,266,412 B2 | 9/2007 | Stypulkowski |
| 7,276,057 B2 | 10/2007 | Gerber |
| 7,288,062 B2 | 10/2007 | Spiegel |
| 7,313,440 B2 | 12/2007 | Miesel |
| 7,324,852 B2 | 1/2008 | Barolat et al. |
| 7,326,181 B2 | 2/2008 | Katims |
| 7,328,068 B2 | 2/2008 | Spinelli et al. |
| 7,333,857 B2 | 2/2008 | Campbell |
| 7,337,005 B2 | 2/2008 | Kim et al. |
| 7,337,006 B2 | 2/2008 | Kim et al. |
| 7,343,200 B2 | 3/2008 | Litvak et al. |
| 7,346,398 B2 | 3/2008 | Gross et al. |
| 7,349,743 B2 | 3/2008 | Tadlock |
| RE40,279 E | 4/2008 | Sluijter et al. |
| 7,359,751 B1 | 4/2008 | Erickson et al. |
| 7,363,076 B2 | 4/2008 | Yun et al. |
| 7,386,341 B2 | 6/2008 | Hafer et al. |
| 7,389,145 B2 | 6/2008 | Kilgore et al. |
| 7,393,351 B2 | 7/2008 | Woloszko et al. |
| 7,433,734 B2 | 10/2008 | King |
| 7,444,181 B2 | 10/2008 | Shi et al. |
| 7,444,183 B2 | 10/2008 | Knudson et al. |
| 7,444,184 B2 | 10/2008 | Boveja et al. |
| 7,447,546 B2 | 11/2008 | Kim et al. |
| 7,450,993 B2 | 11/2008 | Kim et al. |
| 7,452,335 B2 | 11/2008 | Wells et al. |
| 7,463,927 B1 | 12/2008 | Chaouat |
| 7,483,747 B2 | 1/2009 | Gliner et al. |
| 7,489,969 B2 | 2/2009 | Knudson et al. |
| 7,493,172 B2 | 2/2009 | Whitehurst et al. |
| 7,496,404 B2 | 2/2009 | Meadows et al. |
| 7,502,651 B2 | 3/2009 | Kim et al. |
| 7,502,652 B2 | 3/2009 | Gaunt et al. |
| 7,551,964 B2 | 6/2009 | Dobak, III |
| 7,571,007 B2 | 8/2009 | Erickson et al. |
| 7,580,753 B2 | 8/2009 | Kim et al. |
| 7,599,737 B2 | 10/2009 | Yomtov et al. |
| 7,610,096 B2 | 10/2009 | McDonald, III |
| 7,613,520 B2 | 11/2009 | De Ridder |
| 7,634,317 B2 | 12/2009 | Ben-David et al. |
| 7,676,269 B2 | 3/2010 | Yun et al. |
| 7,689,276 B2 | 3/2010 | Dobak |
| 7,689,289 B2 | 3/2010 | King |
| 7,711,432 B2 | 5/2010 | Thimineur et al. |
| 7,715,915 B1 | 5/2010 | Ryu et al. |
| 7,734,340 B2 | 6/2010 | De Ridder |
| 7,734,352 B2 | 6/2010 | Greenberg et al. |
| 7,734,355 B2 | 6/2010 | Cohen et al. |
| 7,742,810 B2 | 6/2010 | Moffitt et al. |
| 7,761,166 B2 | 7/2010 | Giftakis et al. |
| 7,761,168 B2 | 7/2010 | Gross |
| 7,761,170 B2 | 7/2010 | Kaplan et al. |
| 7,769,463 B2 | 8/2010 | Katsnelson |
| 7,778,704 B2 | 8/2010 | Rezai |
| 7,792,591 B2 | 9/2010 | Rooney et al. |
| 7,801,604 B2 | 9/2010 | Brockway et al. |
| 7,805,197 B2 | 9/2010 | Bradley |
| 7,809,443 B2 | 10/2010 | Giftakis et al. |
| 7,813,803 B2 | 10/2010 | Heruth et al. |
| 7,813,804 B1 | 10/2010 | Jaax |
| 7,826,901 B2 | 11/2010 | Lee et al. |
| 7,831,306 B2 | 11/2010 | Finch et al. |
| 7,844,338 B2 | 11/2010 | Knudson et al. |
| 7,848,818 B2 | 12/2010 | Barolat et al. |
| 7,853,322 B2 | 12/2010 | Bourget et al. |
| 7,860,570 B2 | 12/2010 | Whitehurst et al. |
| 7,865,243 B1 | 1/2011 | Whitehurst et al. |
| 7,877,136 B1 | 1/2011 | Moffitt et al. |
| 7,877,146 B2 | 1/2011 | Rezai |
| 7,881,805 B2 | 2/2011 | Bradley |
| 7,890,163 B2 | 2/2011 | Belalcazar |
| 7,890,166 B2 | 2/2011 | Heruth et al. |
| 7,890,176 B2 | 2/2011 | Jaax et al. |
| 7,890,182 B2 | 2/2011 | Parramon et al. |
| 7,890,185 B2 | 2/2011 | Cohen et al. |
| 7,894,907 B2 | 2/2011 | Cowan et al. |
| 7,899,542 B2 | 3/2011 | Cowan et al. |
| 7,914,452 B2 | 3/2011 | Hartley et al. |
| 7,933,654 B2 | 4/2011 | Merfeld et al. |
| 7,937,145 B2 | 5/2011 | Dobak |
| 7,957,797 B2 | 6/2011 | Bourget et al. |
| 7,979,133 B2 | 7/2011 | Feler et al. |
| 8,000,794 B2 | 8/2011 | Lozano |
| 8,010,198 B2 | 8/2011 | Libbus et al. |
| 8,019,423 B2 | 9/2011 | Possover |
| 8,027,718 B2 | 9/2011 | Spinner et al. |
| 8,046,075 B2 | 10/2011 | Rezai |
| 8,060,208 B2 | 11/2011 | Kilgore et al. |
| 8,082,039 B2 | 12/2011 | Kim et al. |
| 8,086,318 B2 | 12/2011 | Strother et al. |
| 8,150,531 B2 | 4/2012 | Skelton |
| 8,170,658 B2 | 5/2012 | Dacey et al. |
| 8,170,675 B2 | 5/2012 | Alataris et al. |
| 8,204,607 B2 | 6/2012 | Rooney et al. |
| 8,209,021 B2 | 6/2012 | Alataris et al. |
| 8,209,028 B2 | 6/2012 | Skelton et al. |
| 8,214,047 B2 | 7/2012 | Pyles et al. |
| 8,224,453 B2 | 7/2012 | De Ridder |
| 8,224,459 B1 | 7/2012 | Pianca et al. |
| 8,255,048 B2 | 8/2012 | Dal Molin et al. |
| 8,255,057 B2 | 8/2012 | Fang et al. |
| 8,280,515 B2 | 10/2012 | Greenspan |
| 8,301,241 B2 | 10/2012 | Ternes et al. |
| 8,340,775 B1 | 12/2012 | Cullen et al. |
| 8,355,792 B2 | 1/2013 | Alataris et al. |
| 8,359,102 B2 | 1/2013 | Alataris et al. |
| 8,359,103 B2 | 1/2013 | Alataris et al. |
| 8,364,271 B2 | 1/2013 | De Ridder |
| 8,364,273 B2 | 1/2013 | De Ridder |
| 8,380,318 B2 | 2/2013 | Kishawi et al. |
| 8,396,559 B2 | 3/2013 | Alataris et al. |
| 8,412,338 B2 | 4/2013 | Faltys |
| 8,423,147 B2 | 4/2013 | Alataris et al. |
| 8,428,735 B2 | 4/2013 | Littlewood et al. |
| 8,428,748 B2 | 4/2013 | Alataris et al. |
| 8,467,875 B2 | 6/2013 | Bennett et al. |
| 8,483,830 B2 | 7/2013 | Tweden |
| 8,509,905 B2 | 8/2013 | Alataris et al. |
| 8,509,906 B2 | 8/2013 | Walker et al. |
| 8,554,326 B2 | 10/2013 | Alataris et al. |
| 8,569,935 B1 | 10/2013 | Kosierkiewicz |
| 8,577,458 B1 | 11/2013 | Libbus et al. |
| 8,612,018 B2 | 12/2013 | Gillbe |
| 8,649,874 B2 | 2/2014 | Alataris et al. |
| 8,666,506 B2 | 3/2014 | King |
| 8,676,331 B2 | 3/2014 | Parker |
| 8,688,212 B2 | 4/2014 | Libbus et al. |
| 8,691,877 B2 | 4/2014 | Yun et al. |
| 8,712,533 B2 | 4/2014 | Alataris et al. |
| 8,718,782 B2 | 5/2014 | Alataris et al. |
| 8,751,009 B2 | 6/2014 | Wacnik |
| 8,768,469 B2 | 7/2014 | Tweden et al. |
| 8,805,512 B1 | 8/2014 | Greiner et al. |
| 8,825,164 B2 | 9/2014 | Tweden et al. |
| 8,825,166 B2 | 9/2014 | John |
| 8,886,326 B2 | 11/2014 | Alataris et al. |
| 8,886,328 B2 | 11/2014 | Alataris et al. |
| 8,892,209 B2 | 11/2014 | Alataris et al. |
| 8,918,172 B2 | 12/2014 | Moffitt et al. |
| 8,918,190 B2 | 12/2014 | Libbus et al. |
| 8,918,191 B2 | 12/2014 | Libbus et al. |

(56) References Cited

U.S. PATENT DOCUMENTS

| | | |
|---|---|---|
| 8,923,964 B2 | 12/2014 | Libbus et al. |
| 8,965,521 B2 | 2/2015 | Birkholz et al. |
| 8,996,125 B2 | 3/2015 | Greiner et al. |
| 9,002,457 B2 | 4/2015 | Hamann et al. |
| 9,002,459 B2 | 4/2015 | Lee et al. |
| 9,026,214 B2 | 5/2015 | Ternes et al. |
| 9,026,215 B2 | 5/2015 | Rossing |
| 9,026,226 B2 | 5/2015 | Gerber et al. |
| 9,067,076 B2 | 6/2015 | Nolan et al. |
| 9,101,770 B2 | 8/2015 | Arcot-Krishnamurthy et al. |
| 9,126,044 B2 | 9/2015 | Kramer et al. |
| 9,132,272 B2 | 9/2015 | Alves et al. |
| 9,180,298 B2 | 11/2015 | Alataris et al. |
| 9,205,258 B2 | 12/2015 | Simon et al. |
| 9,211,410 B2 | 12/2015 | Levine et al. |
| 9,295,840 B1 | 3/2016 | Thacker |
| 9,308,370 B2 | 4/2016 | Lima et al. |
| 9,327,127 B2 | 5/2016 | Alataris et al. |
| 9,370,659 B2 | 6/2016 | Franke et al. |
| 9,381,356 B2 | 7/2016 | Parker |
| 9,403,007 B2 | 8/2016 | Moekelke et al. |
| 9,421,355 B2 | 8/2016 | Colbom |
| 9,440,074 B2 | 9/2016 | Ternes et al. |
| 9,480,846 B2 | 11/2016 | Strother |
| 9,533,153 B2 | 1/2017 | Libbus et al. |
| 9,561,366 B2 | 2/2017 | Wei et al. |
| 9,561,370 B2 | 2/2017 | Rezai |
| 9,572,983 B2 | 2/2017 | Levine et al. |
| 9,694,183 B2 | 7/2017 | Grandhe |
| 9,724,509 B2 | 8/2017 | Su et al. |
| 9,724,511 B2 | 8/2017 | Wei et al. |
| 9,833,614 B1 | 12/2017 | Gliner |
| 9,895,532 B2 | 2/2018 | Kaula et al. |
| 9,895,539 B1 * | 2/2018 | Heit .................. A61N 1/36071 |
| 9,913,980 B2 | 3/2018 | Ostroff et al. |
| 9,950,173 B2 | 4/2018 | Doan |
| 9,968,732 B2 | 5/2018 | Drew et al. |
| 10,188,856 B1 | 1/2019 | Libbus et al. |
| 10,220,205 B2 | 3/2019 | Bhadra et al. |
| 10,328,264 B2 | 6/2019 | Hamann et al. |
| 10,485,975 B2 | 11/2019 | Greiner et al. |
| 10,561,845 B2 | 2/2020 | Giftakis et al. |
| 10,632,300 B2 | 4/2020 | Wagenbach et al. |
| 10,675,468 B2 | 6/2020 | Torgerson |
| 10,898,714 B2 | 1/2021 | Libbus et al. |
| 11,045,649 B2 | 6/2021 | Wei et al. |
| 2002/0055779 A1 | 5/2002 | Andrews |
| 2002/0087201 A1 | 7/2002 | Firlik et al. |
| 2002/0128700 A1 | 9/2002 | Cross |
| 2002/0198572 A1 | 12/2002 | Weiner |
| 2003/0018368 A1 | 1/2003 | Ansarinia |
| 2003/0100931 A1 | 5/2003 | Mullett |
| 2003/0120323 A1 | 6/2003 | Meadows et al. |
| 2003/0135248 A1 | 7/2003 | Stypulkowski |
| 2003/0181958 A1 | 9/2003 | Dobak |
| 2003/0212440 A1 | 11/2003 | Boveja |
| 2004/0015202 A1 | 1/2004 | Chandler et al. |
| 2004/0034394 A1 | 2/2004 | Woods et al. |
| 2004/0039425 A1 | 2/2004 | Greenwood-Van Meerveld |
| 2004/0059395 A1 | 3/2004 | North et al. |
| 2004/0073273 A1 | 4/2004 | Gluckman et al. |
| 2004/0093093 A1 | 5/2004 | Andrews |
| 2004/0116977 A1 | 6/2004 | Finch et al. |
| 2004/0122477 A1 * | 6/2004 | Whitehurst .......... A61N 1/37205 607/9 |
| 2004/0158119 A1 | 8/2004 | Osorio et al. |
| 2004/0158298 A1 | 8/2004 | Gliner |
| 2004/0162590 A1 | 8/2004 | Whitehurst et al. |
| 2004/0167584 A1 | 8/2004 | Carroll et al. |
| 2004/0172085 A1 | 9/2004 | Knudson et al. |
| 2004/0176812 A1 | 9/2004 | Knudson et al. |
| 2004/0186532 A1 | 9/2004 | Tadlock |
| 2004/0193228 A1 | 9/2004 | Gerber |
| 2004/0193230 A1 | 9/2004 | Overstreet |
| 2004/0210270 A1 | 10/2004 | Erickson |
| 2004/0210271 A1 | 10/2004 | Campen et al. |
| 2004/0267330 A1 | 12/2004 | Lee et al. |
| 2005/0021104 A1 | 1/2005 | DiLorenzo |
| 2005/0033381 A1 | 2/2005 | Carter et al. |
| 2005/0038489 A1 | 2/2005 | Grill |
| 2005/0060001 A1 | 3/2005 | Singhal et al. |
| 2005/0070982 A1 | 3/2005 | Heruth et al. |
| 2005/0113877 A1 | 5/2005 | Spinelli et al. |
| 2005/0113878 A1 | 5/2005 | Gerber |
| 2005/0113882 A1 | 5/2005 | Cameron et al. |
| 2005/0119713 A1 | 6/2005 | Whitehurst et al. |
| 2005/0143783 A1 | 6/2005 | Boveja |
| 2005/0143789 A1 | 6/2005 | Whitehurst et al. |
| 2005/0149148 A1 | 7/2005 | King |
| 2005/0153885 A1 | 7/2005 | Yun et al. |
| 2005/0154435 A1 | 7/2005 | Stern et al. |
| 2005/0182453 A1 | 8/2005 | Whitehurst et al. |
| 2005/0187591 A1 | 8/2005 | Carter et al. |
| 2005/0222641 A1 | 10/2005 | Pless |
| 2005/0228451 A1 | 10/2005 | Jaax et al. |
| 2005/0240241 A1 | 10/2005 | Yun et al. |
| 2005/0245978 A1 | 11/2005 | Varrichio et al. |
| 2005/0245987 A1 | 11/2005 | Woods |
| 2005/0246006 A1 | 11/2005 | Daniels |
| 2005/0267545 A1 | 12/2005 | Cory |
| 2005/0278000 A1 | 12/2005 | Strother et al. |
| 2005/0288721 A1 | 12/2005 | Girouard |
| 2006/0004422 A1 | 1/2006 | De Ridder |
| 2006/0009820 A1 | 1/2006 | Royle |
| 2006/0015153 A1 | 1/2006 | Gliner et al. |
| 2006/0025832 A1 | 2/2006 | O'Keeffe et al. |
| 2006/0030895 A1 | 2/2006 | Simon et al. |
| 2006/0030899 A1 | 2/2006 | O'Keeffe et al. |
| 2006/0041285 A1 | 2/2006 | Johnson |
| 2006/0052836 A1 | 3/2006 | Kim et al. |
| 2006/0069415 A1 | 3/2006 | Cameron et al. |
| 2006/0074450 A1 | 4/2006 | Boveja et al. |
| 2006/0079936 A1 | 4/2006 | Boveja et al. |
| 2006/0079937 A1 | 4/2006 | King et al. |
| 2006/0095088 A1 | 5/2006 | De Ridder |
| 2006/0100671 A1 | 5/2006 | Ridder |
| 2006/0149337 A1 | 7/2006 | John |
| 2006/0161219 A1 | 7/2006 | Mock et al. |
| 2006/0161235 A1 | 7/2006 | King |
| 2006/0167498 A1 | 7/2006 | DiLorenzo |
| 2006/0167525 A1 | 7/2006 | King |
| 2006/0168805 A1 | 8/2006 | Hegland et al. |
| 2006/0190044 A1 | 8/2006 | Libbus et al. |
| 2006/0190048 A1 | 8/2006 | Gerber |
| 2006/0206166 A1 | 9/2006 | Weiner |
| 2006/0224187 A1 | 10/2006 | Bradley et al. |
| 2006/0229687 A1 | 10/2006 | Goetz et al. |
| 2006/0253174 A1 | 11/2006 | King |
| 2006/0253182 A1 | 11/2006 | King |
| 2006/0271108 A1 | 11/2006 | Libbus et al. |
| 2007/0021801 A1 | 1/2007 | Heruth et al. |
| 2007/0021803 A1 | 1/2007 | Deem et al. |
| 2007/0025608 A1 | 2/2007 | Armstrong |
| 2007/0027486 A1 | 2/2007 | Armstrong |
| 2007/0032827 A1 | 2/2007 | Katims |
| 2007/0039625 A1 | 2/2007 | Heruth et al. |
| 2007/0043400 A1 | 2/2007 | Donders et al. |
| 2007/0049988 A1 | 3/2007 | Carbunaru |
| 2007/0049991 A1 | 3/2007 | Klostermann et al. |
| 2007/0060954 A1 | 3/2007 | Cameron et al. |
| 2007/0060955 A1 | 3/2007 | Strother et al. |
| 2007/0066995 A1 | 3/2007 | Strother et al. |
| 2007/0066997 A1 | 3/2007 | He et al. |
| 2007/0073353 A1 | 3/2007 | Rooney et al. |
| 2007/0073354 A1 | 3/2007 | Knudson et al. |
| 2007/0083240 A1 | 4/2007 | Peterson et al. |
| 2007/0100388 A1 | 5/2007 | Gerber |
| 2007/0106337 A1 | 5/2007 | Errico et al. |
| 2007/0106342 A1 | 5/2007 | Schumann |
| 2007/0142863 A1 | 6/2007 | Bradley |
| 2007/0150029 A1 | 6/2007 | Bourget et al. |
| 2007/0156183 A1 | 7/2007 | Rhodes |
| 2007/0156207 A1 | 7/2007 | Kothandaraman et al. |
| 2007/0167992 A1 | 7/2007 | Carley |

(56) References Cited

U.S. PATENT DOCUMENTS

| | | |
|---|---|---|
| 2007/0179558 A1 | 8/2007 | Gliner et al. |
| 2007/0179559 A1 | 8/2007 | Giftakis et al. |
| 2007/0179579 A1 | 8/2007 | Feler et al. |
| 2007/0191906 A1 | 8/2007 | Iyer et al. |
| 2007/0203537 A1 | 8/2007 | Goetz et al. |
| 2007/0208381 A1 | 9/2007 | Hill et al. |
| 2007/0208394 A1 | 9/2007 | King et al. |
| 2007/0213789 A1 | 9/2007 | Nolan et al. |
| 2007/0233194 A1 | 10/2007 | Craig |
| 2007/0239226 A1 | 10/2007 | Overstreet |
| 2007/0244522 A1 | 10/2007 | Overstreet |
| 2007/0255118 A1 | 11/2007 | Miesel et al. |
| 2007/0255333 A1 | 11/2007 | Giftakis et al. |
| 2007/0255340 A1 | 11/2007 | Giftakis et al. |
| 2007/0255341 A1 | 11/2007 | Giftakis et al. |
| 2007/0265681 A1 | 11/2007 | Gerber et al. |
| 2007/0282376 A1 | 12/2007 | Shuros et al. |
| 2007/0293893 A1 | 12/2007 | Stolen et al. |
| 2007/0293915 A1 | 12/2007 | Kilgore et al. |
| 2007/0299482 A1 | 12/2007 | Littlewood et al. |
| 2008/0033511 A1 | 2/2008 | Dobak |
| 2008/0058871 A1 | 3/2008 | Libbus et al. |
| 2008/0058878 A1 | 3/2008 | King |
| 2008/0058888 A1 | 3/2008 | King |
| 2008/0065158 A1 | 3/2008 | Ben-Ezra |
| 2008/0086036 A1 | 4/2008 | Hartley et al. |
| 2008/0103570 A1 | 5/2008 | Gerber |
| 2008/0109045 A1 | 5/2008 | Gross et al. |
| 2008/0154329 A1 | 6/2008 | Pyles et al. |
| 2008/0154333 A1 | 6/2008 | Knudson et al. |
| 2008/0167697 A1 | 7/2008 | Johnson |
| 2008/0183259 A1 | 7/2008 | Bly et al. |
| 2008/0234791 A1 | 9/2008 | Arle et al. |
| 2008/0262411 A1 | 10/2008 | Dobak |
| 2008/0269854 A1 | 10/2008 | Hegland et al. |
| 2008/0281381 A1 | 11/2008 | Gerber et al. |
| 2008/0300449 A1 | 12/2008 | Gerber |
| 2008/0319511 A1 | 12/2008 | Pless |
| 2008/0319514 A1 | 12/2008 | Shi et al. |
| 2009/0018617 A1 | 1/2009 | Skelton et al. |
| 2009/0024186 A1 | 1/2009 | Brockway et al. |
| 2009/0024187 A1 | 1/2009 | Erickson et al. |
| 2009/0036945 A1 | 2/2009 | Chancellor et al. |
| 2009/0054950 A1 | 2/2009 | Stephens |
| 2009/0054962 A1 | 2/2009 | Lefler et al. |
| 2009/0069803 A1 | 3/2009 | Starkebaum |
| 2009/0076565 A1 | 3/2009 | Surwit |
| 2009/0083070 A1 | 3/2009 | Giftakis |
| 2009/0112282 A1 | 4/2009 | Kast et al. |
| 2009/0118777 A1* | 5/2009 | Iki ............... A61N 1/36007 607/2 |
| 2009/0125079 A1 | 5/2009 | Armstrong et al. |
| 2009/0132010 A1 | 5/2009 | Kronberg |
| 2009/0132016 A1 | 5/2009 | Putz |
| 2009/0157141 A1 | 6/2009 | Chiao et al. |
| 2009/0157149 A1 | 6/2009 | Wahlgren et al. |
| 2009/0157183 A1 | 6/2009 | Song |
| 2009/0196472 A1 | 8/2009 | Goetz et al. |
| 2009/0198306 A1 | 8/2009 | Goetz et al. |
| 2009/0204173 A1 | 8/2009 | Fang et al. |
| 2009/0204192 A1 | 8/2009 | Carlton et al. |
| 2009/0264959 A1 | 10/2009 | Lange |
| 2009/0264973 A1 | 10/2009 | Boling et al. |
| 2009/0281595 A1 | 11/2009 | King et al. |
| 2009/0287035 A1 | 11/2009 | Dietrich et al. |
| 2009/0287274 A1 | 11/2009 | De Ridder |
| 2009/0287279 A1 | 11/2009 | Parramon et al. |
| 2009/0326611 A1 | 12/2009 | Gillbe |
| 2010/0010567 A1 | 1/2010 | Deem et al. |
| 2010/0016929 A1 | 1/2010 | Prochazka |
| 2010/0023103 A1 | 1/2010 | Elborno |
| 2010/0036454 A1 | 2/2010 | Bennett et al. |
| 2010/0042170 A1 | 2/2010 | Shuros et al. |
| 2010/0042193 A1 | 2/2010 | Slavin |
| 2010/0057178 A1 | 3/2010 | Simon |
| 2010/0094375 A1 | 4/2010 | Donders et al. |
| 2010/0125313 A1 | 5/2010 | Lee et al. |
| 2010/0137938 A1* | 6/2010 | Kishawi ............... A61N 1/0551 607/46 |
| 2010/0152817 A1 | 6/2010 | Gillbe |
| 2010/0228310 A1 | 9/2010 | Shuros et al. |
| 2010/0241190 A1 | 9/2010 | Kilgore et al. |
| 2010/0249876 A1 | 9/2010 | Giftakis et al. |
| 2010/0256696 A1 | 10/2010 | Schleicher et al. |
| 2010/0262205 A1 | 10/2010 | De Ridder |
| 2010/0274312 A1 | 10/2010 | Alataris et al. |
| 2010/0274315 A1 | 10/2010 | Alataris et al. |
| 2010/0274316 A1 | 10/2010 | Alataris et al. |
| 2010/0274317 A1 | 10/2010 | Parker et al. |
| 2010/0274318 A1 | 10/2010 | Walker et al. |
| 2010/0274320 A1 | 10/2010 | Torgerson |
| 2010/0274326 A1 | 10/2010 | Chitre et al. |
| 2010/0318157 A1 | 12/2010 | Giftakis et al. |
| 2010/0324630 A1 | 12/2010 | Lee et al. |
| 2010/0331916 A1 | 12/2010 | Parramon et al. |
| 2011/0009919 A1 | 1/2011 | Carbunaru et al. |
| 2011/0009923 A1 | 1/2011 | Lee |
| 2011/0009927 A1 | 1/2011 | Parker et al. |
| 2011/0022114 A1 | 1/2011 | Navarro |
| 2011/0040291 A1 | 2/2011 | Weissenrieder-Norlin et al. |
| 2011/0040362 A1 | 2/2011 | Godara et al. |
| 2011/0046696 A1 | 2/2011 | Barolat et al. |
| 2011/0077721 A1 | 3/2011 | Whitehurst et al. |
| 2011/0093042 A1 | 4/2011 | Torgerson et al. |
| 2011/0106208 A1 | 5/2011 | Faltys et al. |
| 2011/0184301 A1 | 7/2011 | Holmstrom et al. |
| 2011/0184486 A1 | 7/2011 | De Ridder |
| 2011/0184488 A1 | 7/2011 | De Ridder |
| 2011/0201977 A1 | 8/2011 | Tass |
| 2011/0276107 A1 | 11/2011 | Simon et al. |
| 2011/0282412 A1 | 11/2011 | Glukhovsky et al. |
| 2012/0010680 A1 | 1/2012 | Wei |
| 2012/0089200 A1 | 4/2012 | Ranu et al. |
| 2012/0150252 A1 | 6/2012 | Feldman et al. |
| 2012/0277833 A1 | 11/2012 | Gerber et al. |
| 2012/0283797 A1 | 11/2012 | De Ridder |
| 2013/0006325 A1 | 1/2013 | Woods et al. |
| 2013/0023951 A1 | 1/2013 | Greenspan |
| 2013/0066411 A1 | 3/2013 | Thacker et al. |
| 2013/0079841 A1 | 3/2013 | Su |
| 2013/0096643 A1 | 4/2013 | Fang et al. |
| 2013/0096644 A1 | 4/2013 | Fang et al. |
| 2013/0110196 A1 | 5/2013 | Alataris et al. |
| 2013/0123879 A1 | 5/2013 | Alataris et al. |
| 2013/0172955 A1 | 7/2013 | Alataris et al. |
| 2013/0204173 A1 | 8/2013 | Kelly et al. |
| 2013/0204321 A1 | 8/2013 | Alataris et al. |
| 2013/0204323 A1 | 8/2013 | Thacker et al. |
| 2013/0204324 A1 | 8/2013 | Thacker et al. |
| 2013/0204338 A1 | 8/2013 | Alataris et al. |
| 2013/0211487 A1 | 8/2013 | Fang et al. |
| 2013/0237948 A1 | 9/2013 | Donders et al. |
| 2013/0238047 A1 | 9/2013 | Libbus et al. |
| 2013/0261695 A1 | 10/2013 | Thacker |
| 2013/0261696 A1 | 10/2013 | Thacker |
| 2013/0289659 A1 | 10/2013 | Nelson |
| 2014/0031896 A1 | 1/2014 | Alataris et al. |
| 2014/0142656 A1 | 5/2014 | Alataris et al. |
| 2014/0142657 A1 | 5/2014 | Alataris et al. |
| 2014/0142658 A1* | 5/2014 | Alataris ............... A61N 1/36071 607/46 |
| 2014/0142659 A1 | 5/2014 | Alataris et al. |
| 2014/0142673 A1 | 5/2014 | Alataris et al. |
| 2014/0316484 A1 | 10/2014 | Edgerton |
| 2014/0343622 A1 | 11/2014 | Alataris et al. |
| 2014/0379044 A1 | 12/2014 | Walker et al. |
| 2015/0012079 A1 | 1/2015 | Goroszeniuk et al. |
| 2015/0018896 A1 | 1/2015 | Alataris et al. |
| 2015/0032181 A1 | 1/2015 | Baynham |
| 2015/0032182 A1 | 1/2015 | Alataris et al. |
| 2015/0032183 A1 | 1/2015 | Alataris et al. |
| 2015/0039049 A1 | 2/2015 | Alataris et al. |
| 2015/0039050 A1 | 2/2015 | Alataris et al. |
| 2015/0045853 A1 | 2/2015 | Alataris et al. |

(56) References Cited

U.S. PATENT DOCUMENTS

| | | |
|---|---|---|
| 2015/0045854 A1 | 2/2015 | Alataris et al. |
| 2015/0051664 A1 | 2/2015 | Alataris et al. |
| 2015/0051665 A1 | 2/2015 | Hershey et al. |
| 2015/0073510 A1 | 3/2015 | Perryman |
| 2015/0217116 A1 | 8/2015 | Parramon et al. |
| 2015/0343220 A1 | 12/2015 | Alataris et al. |
| 2016/0114165 A1 | 4/2016 | Levine et al. |
| 2016/0121119 A1 | 5/2016 | Alataris et al. |
| 2016/0256689 A1 | 9/2016 | Vallejo et al. |
| 2016/0263376 A1 | 9/2016 | Yoo et al. |
| 2016/0287872 A1 | 10/2016 | Alataris et al. |
| 2016/0287873 A1 | 10/2016 | Alataris et al. |
| 2016/0287874 A1 | 10/2016 | Alataris et al. |
| 2016/0287875 A1 | 10/2016 | Thacker et al. |
| 2016/0287888 A1 | 10/2016 | Alataris et al. |
| 2016/0303374 A1 | 10/2016 | Alataris et al. |
| 2016/0339239 A1 | 11/2016 | Yoo et al. |
| 2017/0050021 A1 | 2/2017 | Cosman, Sr. |
| 2017/0087369 A1 | 3/2017 | Bokil |
| 2017/0095669 A1 | 4/2017 | Libbus et al. |
| 2017/0165485 A1 | 6/2017 | Sullivan et al. |
| 2017/0209699 A1 | 7/2017 | Thacker et al. |
| 2017/0216602 A1 | 8/2017 | Waataja et al. |
| 2017/0239470 A1 | 8/2017 | Wei et al. |
| 2017/0274209 A1 | 9/2017 | Edgerton |
| 2017/0348526 A1 | 12/2017 | Southwell |
| 2018/0256906 A1 | 9/2018 | Pivonka |
| 2018/0272132 A1 | 9/2018 | Subbaroyan |
| 2019/0321641 A1 | 10/2019 | Baldoni |
| 2020/0139138 A1 | 5/2020 | Sit |
| 2021/0060338 A1 | 3/2021 | Thacker et al. |

FOREIGN PATENT DOCUMENTS

| | | |
|---|---|---|
| EP | 1181947 A2 | 2/2002 |
| EP | 2243511 A2 | 10/2010 |
| EP | 2448633 A1 | 5/2012 |
| EP | 2630984 A1 | 8/2013 |
| GB | 2449546 A | 11/2008 |
| JP | 2002200179 A | 7/2002 |
| JP | 2007528774 A | 10/2007 |
| JP | 2008500086 A | 1/2008 |
| SU | 1512625 A1 | 10/1989 |
| SU | 1690727 A1 | 11/1991 |
| WO | WO-02065896 A2 | 8/2002 |
| WO | WO-02/085448 | 10/2002 |
| WO | WO-02092165 A1 | 11/2002 |
| WO | WO-03015863 A2 | 2/2003 |
| WO | WO-03066154 A2 | 8/2003 |
| WO | WO-2004007018 A1 | 1/2004 |
| WO | WO-2005115532 A2 | 12/2005 |
| WO | WO-2006007048 | 1/2006 |
| WO | WO-2006057734 A1 | 6/2006 |
| WO | WO-2006063458 | 6/2006 |
| WO | WO-2006084635 A2 | 8/2006 |
| WO | WO-2006119046 A1 | 11/2006 |
| WO | WO-2007035925 A2 | 3/2007 |
| WO | WO-2007082382 A1 | 7/2007 |
| WO | WO-2007103324 A1 | 9/2007 |
| WO | WO-2007117232 A1 | 10/2007 |
| WO | WO-2008039982 A2 | 4/2008 |
| WO | WO-2008045434 A2 | 4/2008 |
| WO | WO-2008106174 A1 | 9/2008 |
| WO | WO-2008121891 A1 | 10/2008 |
| WO | WO-2008140940 | 11/2008 |
| WO | WO-2008142402 A1 | 11/2008 |
| WO | WO-2008153726 A2 | 12/2008 |
| WO | WO-2009018518 A1 | 2/2009 |
| WO | WO-2009061813 A1 | 5/2009 |
| WO | WO-2009097224 A1 | 8/2009 |
| WO | WO-2009129329 A1 | 10/2009 |
| WO | WO-2010111358 A2 | 9/2010 |
| WO | WO-2011014570 A1 | 2/2011 |
| WO | WO-2012154985 | 11/2012 |
| WO | WO-2016154091 A1 | 9/2016 |
| WO | WO-2017044904 | 3/2017 |
| WO | WO-2017146658 | 8/2017 |

OTHER PUBLICATIONS

Acticare.com website, http://web.archive.org/web/*/acticare.com, Internet Archive Way Back Machine, 2012, 22 pages.

Advanced Neuromodulation Systems, Compustim SCS Systems, Clinical Manual, 1997, 52 pages.

Agnew et al., "Considerations for safety with chronically implanted nerve electrodes," Epilepsia, 31 .s2, 1990, 6 pages.

Al-Kaisy et al., "10 kHz High-Frequency Spinal Cord Stimulation for Chronic Axial Low Back Pain in Patients With No History of Spinal Surgery: A Preliminary, Prospective, Open Label and Proof-of-Concept Study," Neuromodulation: Technology at the Neural Interface, 2016, 8 pages.

Al-Kaisy et al., "Sustained Effectiveness of 10kHz High-Frequency Spinal Cord Stimulation for Patients with Chronic, Low Back Pain: 24-month Results of Prospective Multicenter Study," Pain Medicine, 2014, 8 pages.

Al-Kaisy et al., "The Use of 10-Kilohertz Spinal Cord Stimulation in a Cohort of Patients with Chronic Neuropathic Limb Pain Refractory to Medical Management," Neuromodulation Technology at the Neural Interface, 2015, 6 pages.

Al-Kaisy et al., Poster: "High-Frequency Spinal Cord Stimulation at 10 kHz for the Treatment of Chronic Back Pain Patients without Prior Back Surgery," 2013, 1 page.

Al-Kaisy., "The use of 10-kilohertz spinal cord stimulation in a cohort of patients with chronic neuropathic limb pain refactory to medical management," Neuromodulation: Technology at the Neural Interface, 18.1, 2015, 6 pages.

Alo et al., "New Trends in Neuromodulation for the Management of Neuropathic Pain," Neurosurgery, vol. 50, No. 4, Apr. 2002, 15 pages.

Augustinsson et al., "Spinal Cord Stimulation in Cardiovascular Disease," Functional Neurosurgery, vol. 6, No. 1, Jan. 1995, 10 pages.

Bara et al., Poster re: High Frequency Spinal Cord Stimulation for Dominant Back Pain—1 year follow up, 2013, 1 page.

Barolat et al., "Multifactorial Analysis of Epidural Spinal Cord Stimulation," Stereotactic and Functional Neurosurgery, 1991 56: 77-103.

Barolat et al., "Spinal Cord Stimulation for Chronic Pain Management," Seminars in Neurosurgery, vol. 15, Nos. 2/3, 2004, 26 pages.

Barolat et al., "Surgical Management of Pain—Spinal Cord Stimulation: Equipment and Implantation Techniques," Chapter 41, Thieme Medical Publishers, New York, 2002, 11 pages.

Bennett et al., "Spinal Cord Stimulation for Complex regional pain syndrome I [RSD]: a Retrospective Multicenter Experience from 1995 to 1998 of 101 patients." Neuromodulation, vol. 2, No. 3, 1999, 9 pages.

Benyamin et al., "A Case of Spinal Cord Stimulation in Raynaud's Phenomenon: Can Subthreshold Sensory Stimulation Have an Effect?" Pain Physician www.painphysicianjournal.com, 2007, 6 pages.

Bhadra et al., "High Frequency electrical conduction block of the pudendal nerve," Journal of Neural Engineering—Institute of Physics Publishing, 2006, 8 pages.

Bhadra et al., Stimulation of High-Frequency Sinusoidal Electrical Block of Mammalian Myelinated Axons, J Comput Neurosco, 22:313-326, 2007.

Bhadra MD, Niloy et al., "High-Frequency Electrical Conduction Block of Mammalian Peripheral Motor Nerve," Muscle and Nerve, Dec. 2005, 9 pages.

BionicNAVIGATOR Software Guide, Part MP9055261-001, 2004, 58 pages.

Boger et al., "Bladder Voiding by Combined High Frequency Electrical Pudendal Nerve Block and Sacral Root Stimulation," Neurourology and Urodynamics, 27, 2008, 5 pages.

Boston Scientific "Precision™ Spinal Cord Stimulator System Clinician Manual—Directions for Use," Clinician Manual, 2015, 74 pages (pp. I, 9-10).

(56) References Cited

OTHER PUBLICATIONS

Boston Scientific, News Release: "New Data Presented at NANS 2014 Demonstrate Long-Term, Low Back Pain Relief with Boston Scientific Precision Spectra™ Spinal Cord Stimulator System," Dec. 12, 2014, 8 pages.
Bowman and McNeal, Response of Single Alpha Motoneurons to High-Frequency Pulse Trains, Appl. Neurophysiol. 49, p. 121-138, 1986, 10 pages.
Broseta et al., "High-Frequency cervical spinal cord stimulation in spasticity and motor disorders," Advances in Stereotactic and Functional Neurosurgery 7. Springer Viennam 1987, 6 pages.
Butt et al., "Histological Findings Using Novel Stimulation Parameters in a Caprine Model," European Journal of Pain Supplements, 2011, 2 pages.
Cahana et al., "Acute Differential Modulation of Synaptic Transmission and Cell Suvival During Exposure to Pulsed and Continuous Radiofrequency Energy," Journal of Pain, vol. 4, No. 4, May 2003, 6 pages.
Cameron et al., "Effects of posture on stimulation parameters in spinal cord stimulation," Neuromodulation: Technology at the Neural Interface 1.4, 1998, 8 pages.
Camilleri et al., "Intra-abdominal vagal blocking (VBLOC therapy): clinical results with a new implantable medical device," Surgery 143.6, 2008, 9 pages.
ClinicalTrials.gov, "Safety and Effectiveness Study of the Precision SCS System Adapted for High-Rate Spinal Cord Stimulation (Accelerate)," https://clinicaltrials.gov/ct2/show/NCT02093793?term=boston+scientific&recr=Open&cond=%22Pain%22&rank=3, Feb. 2015, 3 pages.
Crapanzano et al., "High Frequency Spinal Cord Stimulation for Complex Regional Pain Syndrome: A Case Report," Pain Physician, 2017, 6 pages.
Crosby et al., "Stimulation Parameters Define the Effectiveness of Burst Spinal Cord Stimulation in a Rat Model of Neuropathic Pain," Neuromodulation Technology at the Neural Interface, International Neuromodulation Society, 2014, 8 pages.
Cuellar et al., "Effect of High Frequency Alternating Current on Spinal Afferent Nociceptive Transmission," Neuromodulation: Technology at the Neural Interface, 2012, 10 pages.
De Carolis et al., Poster: "Efficacy of Spinal Cord Stimulation (SCS) in the Treatment of Failed Back Surgery Syndrome (FBSS): a comparative study," 2013, 1 page.
DeRidder et al., "Are Paresthesias necessary for pain suppression in SCS—Burst Stimulation," BRAIN, Brain Research Center Antwerp of Innovative and Interdisciplinary Neuromodulation, 2010, 27 pages.
DeRidder et al., "Burst Spinal Cord Stimulation: Toward Paresthesia-Free Pain Suppression," www.neurosurgery-online.com, vol. 66, Nos. 5, May 2010, 5 pages.
Dorland's Illustrated Medical Dictionary, Twenty-sixth Edition, "Paresthesia," 1981, 4 pages.
Doug Atkins of Medtronic Neurological, "Medtronic Neurostimulation Leads, 510(k) Summary," Submission Prepared: Feb. 27, 2004, 6 pages.
Duyvendak et al., "Spinal Cord Stimulation With a Dual Quadripolar Surgical Lead Placed in General Anesthesia is Effective in Treating Intractable Low Back and Leg Pain," Neuromodulation: Technology at the Neural Interface, vol. 10, No. 2, 2007, 7 pages.
Eddicks et al., "Thoracic Spinal Cord Stimulation Improves Functional Status and Relieves Symptoms in Patients with Refractory Angina Pectoris: The First Placebo-Controlled Randomised Study," Heart Journal, 2007, 6 pages.
Feeling vs. Function Poster, Mager and Associates Consulting, 2009, 1 page.
Geddes, "A Short History of the electrical stimulation of excitable tissue—Including Electrotherapeutic Applications," The Physiologist, vol. 27, No. 1, Feb. 1984, 51 pages.
Grill, Warren et al., "Stimulus Waveforms for Selective Neural Stimulation," IEEE Engineering in Medicine and Biology, Jul./Aug. 1995, pp. 375-385.

Gulve et al., Poster re: "High-Frequency Spinal Cord Stimulation at 10kHz for the Treatment of Chronic Back Pain Patients without Prior Back Surgery."
Gulve et al., Poster: "10kHz High Frequency Spinal Cord Stimulation: Middlesbrough Experience," 2013, 1 page.
Guo et al., "Design and Implement of a Mini-Instrument for Rehabilitation with Transcutaneous Electrical Nerve Stimulation," School of Medical Instrument and Food Engineering, University of Shanghai for Science and Technology, Shanghai China, Mar. 31, 2007, 5 pages.
Hefferman et al., "Efficacy of Transcutaneous Spinal Electroanalgesia in Acute Postoperative Pain Management," Anesthesiology, 2001, 2 pages.
Higuchi et al., "Exposure of the Dorsal Root Ganglion in Rats to Pulsed Radiofrequency Currents Activates Dorsal Horn Lamina I and II Neurons," Neurosurgery, vol. 50, No. 4, Apr. 2002, 7 pages.
Hilberstadt et al., "The Effect of Transcutaneous Spinal Electroanalgesia upon Chronic Pain: A single case study," Physiotherapy, vol. 86 No. 3, Mar. 2000, 2 pages.
Hopp et al., "Effect of anodal blockade of myelinated fibers on vagal c-fiber afferents," American Journal Physiological Society, Nov. 1980 239(5), 9 pages.
Hoppenstein, Reuben, "Electrical Stimulation of the Ventral and Dorsal Columns of the Spinal Cord for Relief of Chronic Intractable Pain: Preliminary Report," Surgical Neurology, vol. 4, No. 1, Jul. 1975, 9 pages.
House et al., "Safety and Efficacy of the House/3M Cochlear Implant in Profoundly Deaf Adults," Otolaryngologic Clinics of North America, vol. 19, No. 2, May 1986, 12 pages.
Huxely et al., "Excitation and Conduction in Nerve: Quantitative Analysis," Science, 1964 Sep. 11 145: 1154-9.
International Neuromodulation Society 10th World Congress, Neuromodulation: Technology that Improves Patient Care, London, England, May 21-26, 2011, 385 pages.
J.P. Morgan North America Equity Research, "Nevro—Let the Launch Begin: Senza Approved, Raising PT to $54," www.jpmorganmarkets.com, May 10, 2015, 8 pages.
J.P. Morgan North America Equity Research, "Nevro—Welcome to the Future of Spinal Cord Stimulation Initiating at OW with $34 Price Target," www.jpmorganmarkets.com, Dec. 1, 2014, 39 pages.
Jacques et al., "Development of a New Implantable Bio-Telestimulator," Surg. Neurol., vol. 13, May 1980, 2 pages.
Jain et al., Abstract—"Accelerate: A Prospective Multicenter Trial Evaluating the Use of High-Rate Spinal Cord Stimulation in the Management of Chronic Intractable Pain," The American Academy of Pain Medicine, 2015, 1 page.
Jang et al., "Analysis of Failed Spinal Cord Stimulation Trails in the Treatment of Intractable Chronic Pain," J. Korean Neurosurg Soc 43, 2008, 5 pages.
Jezernik et al., "Electrical Stimulation for the Treatment of Bladder Dysfunction: Current Status and Future Possibilities," Neurological Research, vol. 24, Jul. 2002, 18 pages.
JMP Securities, "Nevro Corp. (NVRO) Initiating Coverage on Nevro Corp. with a Market Outperform Rating—Investment Highlights," Dec. 1, 2014, 42 pages.
Kapural et al., "Comparison of 10-kHz High Frequency and Traditional Low-Frequency Spinal Cord Stimulation for the Treatment of Chronic Back and Leg Pain: 24-Month Results From a Multicenter, Randomized, Controlled Pivotal Trial," Neurosurgery, vol. 79, No. 5, Nov. 2016, 11 pages.
Kapural et al., "Novel 10-Khz High Frequency Therapy (HF10 Therapy) is Superior to Traditional Low-Frequency Spinal Cord Stimulation for Treatment of Chronic Back and Leg Pain," Anesthesiology The Journal of American Society of Anesthesiologists, Inc., 2005, 11 pages.
Kilgore et al. "Nerve Conduction Block Utilizing High-Frequency Alternating Current" Medical & Biology Engineering and Computing, 2004, vol. 42, pp. 394-406.
Kilgore et al. "Reversible Nerve Conduction Block Using Kilohertz Frequency Alternating Current," Neuromodulation Technology at the Neural Interface, International Neuromodulation Society, 2013, 13 pages.

(56) References Cited

OTHER PUBLICATIONS

Kreitler et al., "Chapter 15: Implantable Devices and Drug Delivery Systems—The Handbook for Chronic Pain," NOVA Biomedical Books, New York, 2007, 17 pages.
Krista Oakes of Neuromed, Inc., "Implanted Spinal Cord Stimulator Lead 510(k) Summary of Safety and Effectiveness," Submission Prepared Feb. 21, 1996, 3 pages.
Kuechmann et al., Abstract #853: "Could Automatic Position Adaptive Stimulation Be Useful in Spinal Cord Stimulation?" Medtronic, Inc., Minneapolis, MN, European Journal of Pain 13, 2009, 1 page.
Kumar et al., "Spinal Cord Stimulation in Treatment of Chronic Benign Pain: Challenges in Treatment Planning and Present Status, a 22-Year Experience," Neurosurgery, vol. 58, No. 3, Mar. 2006, 16 pages.
Kumar et al., "The Effects of Spinal Cord Stimulation in Neuropathic Pain Are Sustained: A 24-month Follow-Up of the Prospective Randomized Controlled Multicenter Trial of the Effectiveness of Spinal Cord Stimulation," www.neurosurgery-online.com, vol. 63, No. 4, Oct. 2008, 9 pages.
Lambru et al., "Safety and Efficacy of Cervical 10 kHz Spinal Cord Stimulation in Chronic Refactory Primary Headaches: A Retrospective Case Series," The Journal of Headache and Pain, 2016, 8 pages.
Lempka et al., "Computational Analysis of Kilohertz Frequency Spinal Cord Stimulation for Chronic Pain Management," Anesthesiology, vol. 122, No. 6, Jun. 2015, 15 pages.
Linderoth et al., "Mechanisms of Spinal Cord Stimulation in Neuropathic and Ischemic Pain Syndromes," Neuromodulation, Chapter 25, 2009, 19 pages.
Linderoth et al., "Mechanisms of Spinal Cord Stimulation in Painful Syndromes: Role of Animal Models," Pain Medicine, vol. 7, No. S1, 2006, 13 pages.
Linderoth et al., "Physiology of Spinal Cord Stimulation: Review and Update," Neuromodulation, vol. 2, No. 3, 1999, 15 pages.
MacDonald, Alexander J. R, and Coates, Tim W., "The Discovery of Transcutaneous Spinal Electroanalgesia and Its Relief of Chronic Pain," Physiotherapy, vol. 81. No. 11, Nov. 1995, 9 pages.
Manola et al., "Technical Performance of Percutaneous Leads for Spinal Cord Stimulation: A Modeling Study," International Neuromodulation Society, 2005, 12 pages.
Mavoori et al., "An Autonomous implantable computer for neural recording and stimulation in unrestrained primates," Journal of Neuroscience Methods, 2005, 7 pages.
Mediati, R.D., , "Mechanisms of Spinal Cord Stimulation," Florence, Oct. 2, 2002, 31 pages.
Medtronic—Neurological Division, QuadPlus, Model 3888, Lead Kit for Spinal Cord Stimulation (SCS) Implant Manual, 1996, 33 pages.
Medtronic—Neurological Division, Resume II, Model 3587A, Lead Kit for Spinal Cord Stimulation (SCS) and Peripheral Nerve Stimulation (PNS), Implant Manual, 1996, 32 pages.
Medtronic—Neurological Division, Resume TL, Model 3986, Lead Kit for Spinal Cord Stimulation (SCS) and Peripheral Nerve Stimulation (PNS), Implant Manual, 1996, 27 pages.
Medtronic—Neurostimulation Systems: Expanding the Array of Pain Control Solutions, 1999, 6 pages.
Medtronic commercial leaflet entitled: Surgical Lead Comparison, 1999, 4 pages.
Medtronic, "Medtronic Pain Therapy—Using Neurostimulation for Chronic Pain, Information for Prescribers" 2007, 29 pages.
Medtronic, Pain Therapy Product Guide, Dec. 2008, 31 pages.
Medtronic, Pisces Quad 3487A, Pisces Quad Compact model 3887, Pisces Quad Plus 3888 Lead Kit, Implant Manual, 2008, 16 pages.
Medtronic: Spinal Cord Stimulation Systems, 2013, 4 pages.
Melzack, Ronald et al., "Pain Mechanisms: A New Theory," Science, vol. 150, No. 3699, Nov. 19, 1965, 9 pages.
Merriam Webster's Collegiate Dictionary, Tenth Edition, definition of "Implantable," 1995, 3 pages.
Meyerson et al., Mechanisms of spinal cord stimulation in neuropathic pain, Neurological Research, vol. 22, Apr. 2000, 5 pages.
Miller, Jonathan, "Neurosurgery Survival Guide—A Comprehensive Guide to Neurosurgical Diagnosis and Treatment," http://d3jonline.tripod.com/neurosurgery/, Nov. 14, 2016, 4 pages.
Miller, Jonathan, "Parameters of Spinal Cord Stimulation and Their Role in Electrical Charge Delivery: A Review," Neuromodulation: Technology at the Neural Interface, 2016, 12 pages.
Morgan Stanley Research North America, "Nevro Corp—There's Something Happening Here," Dec. 15, 2014, 12 pages.
Mosby's Medical Dictionary, 8th Edition, "Paresthesia," 2009, 3 pages.
Mounaïm et al., "New Neurostimulation Strategy and Corresponding Implantable Device to Enhance Bladder Functions," Biomedical Engineering Trends in Electronics, Communications and Software, Chapter 5, 2011, 15 pages.
Mueller et al., "The MED-EL SONATATI 100 Cochlear Implant: An evaluation of its safety in adults and children," Acta Oto-Laryngologica, vol. 131, No. 5, 2011, 8 pages.
Muller and Hunsperger, "Helvetica Physiologica Acta—Reversible Blockierung der Erregungsleitung im Nerven durch Mittelfrequenz-Daverstrom," Schwabe & Co. Basel, vol. 25, Fasc. 1, 1967, 4 pages.
Munglani, Rajesh, "The Longer Term Effect of Pulsed Radiofrequency for Neuropathic Pain," Pain 80, 1999, 3 pages.
Nashold et al., "Dorsal Column Stimulation for Control Pain—Preliminary Report on 30 Patients," J. Neurosurg., vol. 36, May 1972, 8 pages.
Nevro—Chronic Pain and Treatments, http://www.nevro.com/English/Patients/Chronic-Pain-and-Treatments/default.aspx 2016, 3 pages.
Nevro—Clinical Evidence www.nevro.com/English/Physicians/Clinical-Evidence/default.aspx, 2016, 2 pages.
Nevro—HF10™ Therapy Fact Sheet, http://www.nevro.com/English/Newsroom/Resources/default.aspx, 2015, 4 pages.
Nevro—Physician Overview www.nevro.com/English/Physicians/Physician-Overview/default.aspx, 2016, 5 pages.
Nevro—Senza System http://www.nevro.com/English/Physicians/Senza-System/default.aspx, 2016, 3 pages.
Nevro HF10 Therapy—New Hope for Chronic Back Pain and Leg Pain Sufferers, http://s21.q4cdn.com/478267292/files/doc_downloads/HF10-Therapy-New-Hope-for-Chronic-Pain.pdf, 2016, 2 pages.
Nevro Senza Patient Manual, Jan. 16, 2015, 53 pages.
Nevro Senza Physician Implant Manual, Jan. 16, 2015, 31 pages.
Nevro website: HF10 Therapy Advantages, www.nevro.com/English/Patients/HF10-Therapy-Advantages/default.aspx, 2016, 3 pages.
Nevro, PMA Approval Letter and Referenced Summary of Safety and Effectiveness Data (SSED) May 8, 2015, 60 pages.
Nevro's presentation of HF10 therapy on Nevro's website, http://www.nevro.com/English/Home/default.aspx, 2016, 2 pages.
News Release Details, "Nevro Corp. Announces Pricing of Initial Public Offering," 2014, 1 page.
NIDCD-NIH 2011, Cochlear Implant Brochure, http://www.nidcd.nih.gov/health/hearing/pages/coch.aspx, Jun. 29, 2012, 2 pages.
North American Neuromodulation Society—14th Annual Meeting, "Neuromodulation: Vision 2010," Dec. 2-5, 2010, 9 pages.
North American Neuromodulation Society—16th Annual Meeting, "From Innovation to Reality Syllabus," Dec. 6-9, 2012, 198 pages.
North American Neuromodulation Society—Celebrating 20 years, 1 8th Annual Meeting Program Book, Dec. 11-14, 2014, 28 pages.
North American Neuromodulation Society, "Today's Vision, Tomorrow's Reality—17th Annual Meeting," Dec. 5-8, 2013, 12 pages.
North American Neuromodulation, "15th Annual Meeting, Our Crystal Anniversary," Dec. 8-11, 2011, 8 pages.
North et al., "Failed Back Surgery Syndrome: 5-year Follow-Up after Spinal Cord Stimulator Implantation," Neurosurgery, Official Journal of the Congress of Neurological Surgeons, vol. 28, No. 5, May 1991, 9 pages.
North et al., "Spinal Cord Stimulation for Axial Low Back Pain," Spine, vol. 30, No. 12, 2005, 7 pages.
North et al., "Spinal Cord Stimulation for Chronic, Intractable Pain: Experience over Two Decades," Neurosurgery, vol. 32, No. 2, Mar. 1993, 12 pages.
North et al., "Spinal Cord Stimulation With Interleaved Pulses: A Randomized, Controlled Trial," vol. 10, No. 4, 2007, 9 pages.

(56) References Cited

OTHER PUBLICATIONS

Oakley et al., "A New Spinal Cord Stimulation System Effectively Relieves Chronic, Intractable Pain: A Multicenter Prospective Clinical Study," Neuromodulation: Technology at the Neural Interface, vol. 10, No. 3, 2007, 17 pages.

Oakley, John C., "Spinal Cord Stimulation in Axial Low Back Pain: Solving the Dilemma," Pain Medicine, vol. 7, No. S1, 2006, 6 pages.

Oakley, John C., "Spinal Cord Stimulation Mechanisms of Action," Spine vol. 27, No. 22, copyright 2002, 10 pages.

OHSIPP Summer Newsletter, The Official Newsletter for the Ohio Society of Interventional Pain Physicians, vol. 1 Ed. 2, Summer 2010, 8 pages.

Paicius et al., "Peripheral Nerve Field Stimulation for the Treatment of Chronic Low Back Pain: Preliminary Results of Long-Term Follow-up: A Case Series," Neuromodulation: Technology at the Neural Interface, vol. 10, No. 3, 2007, 12 pages.

Palmer et al., "Transcutaneous electrical nerve stimulation and transcutaneous spinal electroanalgesia: A preliminary efficacy and mechanisms-based investigation," Physiotherapy, 95, 2009, 7 pages.

Perruchoud et al., "Analgesic Efficacy of High-Frequency Spinal Cord Stimulation: A Randomized Double-Blind Placebo-Controlled Study," Neuromodulation: Technology at Neural Interface, International Neuromodulation Society, 2013, 7 pages.

Prausnitz et al., "The Effects of Electric Current Applied to Skin: A Review for Transdermal Drug Delivery," Advanced Drug Delivery Reviews 18, 1996, 31 pages.

Precision—Charging System, Advanced Bionic Corporation, Part 9055259-0001, 2005, 2 pages.

Precision—Physician System Handbook, Advanced Bionic Corporation, Part 9055253-0001, 2005, 92 pages.

Precision—Physician Trail Kit Insert, Advanced Bionic Corporation, Part 9055258-0001, 2005, 2 pages.

Precision Spinal Cord Stimulation—Charging System Insert, Advanced Bionic Corporation, Part 9055074-0001, 2004, 2 pages.

Precision Spinal Cord Stimulation—Patienet Trial Journal, Advanced Bionic Corporation, Part 9055260-0001, 2004, 10 pages.

Precision Spinal Cord Stimulation—Patient System Handbook, Advanced Bionic Corporation, Part 9055072-0001, 2004, 93 pages.

Precision Spinal Cord Stimulation—Physician Implant Manual, Advanced Bionic Corporation, Part 9055100, 2004, 62 pages.

Precision Spinal Cord Stimulation—Physician Implant Manual, Advanced Bionic Corporation, Part 9055255-0001, 2005, 70 pages.

Precision Spinal Cord Stimulation—Physician Lead Manual, Advanced Bionic Corporation, Part No. 9055183-001, May 2004, 31 pages.

Precision Spinal Cord Stimulation—Physician Lead Manual, Advanced Bionic Corporation, Part 9055095, 2004, 62 pages.

Precision Spinal Cord Stimulation—Physician Lead Manual, Advanced Bionic Corporation, Part 9055256-0001, 2005, 56 pages.

Precision Spinal Cord Stimulation—Physician Trail Handbook, Advanced Bionic Corporation, Part 9055254-0001, 2005, 66 pages.

Precision Spinal Cord Stimulation—Physician Trail Kit Model SC-7005, Part 9055066-001, Advanced Bionic Corporation, 2004, 2 pages.

Precision Spinal Cord Stimulation—Remote Control Model SC-5200, Part 9055107-001, 2004, Advanced Bionic Corporation, 2 pages.

Precision Spinal Cord Stimulation—Remote Control Model SC-5210, Advanced Bionic Corporation, Part 9055257-001, 2005, 2 pages.

Precision Spinal Cord Stimulation System—Patient System Handbook, Advanced Bionic Corporation, Part No. 9055184-001, May 2004, 86 pages.

Precision Spinal Cord Stimulation System, Patient Trial Handbook, Part 9055078, 2004, 74 pages.

Pudenz et al., "Development of an Implantable Telestimulator," Proc. 4th Ann. Nat'l Conf. Neuroelectric Soc., Mar. 10-12, 1971, 111-12 (Wulfsohn, Norman L. and Anthony Sances, Jr. (eds.) 1971, 4 pages.

Pudenz et al., "Neural Stimulation: Clinical and Laboratory Experiences," Surg. Neurol, 39:235-242 (1993).

Rapcan et al., Clinical Study, "High-Frequency—Spinal Cord Stimulation," Indexed and Abstracted in Science Citation Index Expanded and in Journal Citation Reports, 2015, 3 pages.

Reddy et al., "Comparison of Conventional and Kilohertz Frequency Epidural Stimulation in Patients Undergoing Trailing for Spinal Cord Stimulation: Clinical Considerations," World Neurosurgery, www.sciencedirect.com, 6 pages, 2015.

Remedi Pain Relief—ENM (Electronic Nerve Modulation), https://web.archive.org/web/20050906181041/http://www.remediuk.com/trials.htm, 2005, 5 pages.

Robb et al., "Transcutaneous Electrical Nerve Stimulation vs. Transcutaneous Spinal Electroanalgesia for Chronic Pain Associated with Breast Cancer Treatments," Journal of Pain and Symptom Management, vol. 33, No. 4, Apr. 2007, 10 pages.

Royle, John., "Transcutaneous Spinal Electroanalgesia and Chronic Pain," Physiotherapy, vol. 86, No. 5, May 2000, 1 page.

Schulman et al., "Battery Powered BION FES Network," Proceedings of the 26th Annual Conference of the IEEE EMBS, San Francisco, CA., Sep. 1-5, 2004, 4 pages.

Science Daily, "Chronic Pain Costs U.S. upto $635 billion, study shows," www.sciencedaily.com/releases/2012/09/120911091100.htm, Sep. 11, 2012, 2 pages.

Senza Spinal Cord Stimulation (SCS) System—P130022, http://www.fda.gov/MedicalDevices/ProductsandMedicalProcedures/DeviceApprovalsandClearances/Recently-ApprovedDevices/ucm449963.htm Oct. 14, 2016, 2 pages.

Sharan et al., "Evolving Patterns of Spinal Cord Stimulation in Patients Implanted for Intractable Low Back and Leg Pain," International Neuromodulation Society, vol. 5, No. 3, 2002, 13 pages.

Shealy et al., "Dorsal Column Electrohypalgesia," Jul. 1969, 8 pages.

Shealy MD, C. Norman et al., "Electrical Inhibition of Pain by Stimulation of the Dorsal Columns: Preliminary Clinical Report," Anesthesiaand Analgesia Current Researches, vol. 446, No. 4, Jul.-Aug. 1967, 3 pages.

Shelden et al., "Depolarization in the Treatment of Trigeminal Neuralgia," Evaluation of Compression and Electrical Methods Clinical Concept of Neurophysiological Mechanism, 1966, 8 pages.

Shelden et al., "Development and Clinical Capabilities of a New Implantable Biostimulator," The American J. of Surgery, vol. 124, Aug. 1972, 6 pages.

Shelden et al., Electrical Control of Facial Pain, Am. J. of Surgery, vol. 114, Aug. 1967, 4 pages.

Shelden et al., "Electrical stimulation of the nervous system," Surg. Neurol. vol. 4, No. 1, Jul. 1975, 6 pages.

Simpson et al., "A Randomized, Double-Blind, Crossover Study of the Use of Transcutaneous Spinal Electroanalgesia in Patients with Pain from Chronic Critical Limb Ischemia," Journal of Pain and Symptom Management, vol. 28, No. 5, Nov. 2004, 6 pages.

Simpson, BA, "Spinal Cord Stimulation in 60 cases of Intractable Pain." Journal of Neurology, Neurosurgery and Psychiatry, 1991 54 pp. 196-199.

Simpson, BA, "Spinal Cord Stimulation." British Journal of Neurosurgery, 1997, Feb. 11 (1), 5-11, 7 pages.

Sluijter et al., "The Effects of Pulsed Radiofrequency Fields Applied to the Dorsal Root Ganglion—A Preliminary Report," The Pain Clinic, vol. 11, No. 2, 1998, 12 pages.

Smet et al,., "Successful Treatment of Low Back Pain with a Novel Neuromodulation Device," AZ Nikolaas, 2010, 12 pages.

Smet et al., Poster: "High-Frequency Spinal Cord Stimulation at 10 kHz after Failed Traditional Spinal Cord Stimulation," NANS, 2013, 1 page.

Solomonow et al., "Control of Muscle Contractile Force through Indirect High-Frequency Stimulation," AM Journal of Physical Medicine, 1983, vol. 62, No. 3, pp. 71-82.

St. Jude Medical, "Eon Mini™ Rechargeable IPG, The smallest, longest lasting IPG for enhanced patient satisfaction," Apr. 29, 2013, 3 pages.

St. Jude Medical, "Individualized Therapy through Diverse Lead Options," 2008, 6 pages.

Stimwave, News Release: Stimwave Receives FDA Approval for High Frequency IDE, http://stimwave.com/newsroom/latest-news, Jun. 9, 2015, 2 pages.

(56) References Cited

OTHER PUBLICATIONS

Struijk et al., "Recruitment of Dorsal Column Fibers in Spinal Cord Stimulation: Influence of Collateral Branching," IEEE Transactions on Biomedical Engineering, vol. 39, No. 9, Sep. 1992, 10 pages.
Sweet et al., "Paresthesia-Free High Density Spinal Cord Stimulation for Postlaminectomy Syndrome in a Prescreened Population: A Prospective Case Series," Neuromodulation: Technology at the Neural Interface, 2015, 7 pages.
Swigris et al., "Implantable Spinal Cord Stimulator to Treat the Ischemic Manifestations of Thromboangiitis Obliterans (Buerger's disease)," Journal of Vascular Surgery, vol. 29, No. 5, 1998, 8 pages.
Tan et al., "Intensity Modulation: A Novel Approach to Percept Control in Spinal Cord Stimulation," Neuromodulation Technology at the Neural Interface, International Neuromodulation Society 2015, 6 pages.
Tanner, J.A., "Reversible blocking of nerve conduction by alternating-current excitation," Nature, 1962, Aug. 18 195: 712-3.
Taylor et al., "The Cost Effectiveness of Spinal Cord Stimulation in the Treatment of Pain: A Systematic Review of the Literature," Journal of Pain and Symptom Management, vol. 27, No. 4., Apr. 2001, 9 pages.
Tesfaye et al., "Electrical Spinal Cord Stimulation for Painful Diabetic Peripheral Neuropathy," The Lancet, vol. 348, Dec. 21-28, 1996, 4 pages.
Thompson et al., "A double blind randomised controlled clinical trial on the effect of transcutaneous spinal electroanalgesia (TSE) on low back pain," European Journal of Pain, vol. 12, Issue 3, Apr. 2008, 6 pages.
Tiede et al., "Novel Spinal Cord Stimulation Parameters in Patients with Predominate Back Pain," Neuromodulation: Technology at the Neural Interface, 2013, 6 pages.
Tollison et al., "Practical Pain Management Neurostimulation Techniques," Chapter 12, Lippincott Williams and Wilkins, Third Edition, 2002, 13 pages.
Towell et al., "High Frequency non-invasive stimulation over the spine: Effects on mood and mechanical pain tolerance in normal subjects," Behavioral Neurology, vol. 10, 1997, 6 pages.
Urban et al., "Percutaneous epidural stimulation of the spinal cord for relief of pain—Long Term Results," Journal of Neurosurgery, vol. 48, Mar. 1978, 7 pages.
Van Butyen et al., "High Frequency Spinal Cord Stimulation for the Treatment of Chronic Back Pain Patients: Results of a Prospective Multicenter European Clinical Study," Neuromodulation Technology at the Neural Interface, International Neuromodulation Society, 2012, 8 pages.
Van Buyten et al., "Pain Relief for Axial Back Pain Patients," INS Meeting Poster, 2011, 1 page.
Van Den Honert et al. "Generation of Unidirectionally Propagated Action Potentials Nerve by Brief Stimuli" Science, vol. 26, pp. 1311-1312.
Van Den Honert, Mortimer JT, "A Technique for Collision Block of Peripheral Nerve: Frequency Dependence," MP-11 IEEE Trans. Biomed, Eng. 28: 379-382, 1981.
Van Havenbergh et al., "Spinal Cord Stimulation for the Treatment of Chronic Back Pain Patients: 500-Hz vs. 1000-Hz Burst Stimulation," Neuromodulation: Technology at the Neural Interface, International Neuromodulation Society, 2014, 4 pages.
Verrills et al., "Peripheral Nerve Field Stimulation for Chronic Pain: 100 Cases and Review of the Literature," Pain Medicine, 2011, 11 pages.
Verrills et al., "Salvaging Failed Neuromodulation Implants with Nevro High Frequency Spinal Cord System,"NANS Poster, 2013, 1 page.
Von Korff et al., "Assessing Global Pain Severity by Self-Report in Clinical and Health Services Research," Spine, vol. 25, No. 24, 2000, 12 pages.
Wallace et al., Poster: "Accelerate: A Prospective Multicenter Trial Evaluating the Use of High-Rate Spinal Cord Stimulation in the Management of Chronic Intractable Pain," Boston Scientific Corporation, 2015, 1 page.
Ward et al., "Electrical Stimulation Using Kilohertz-Frequency Alternating Current," Journal of the American Physical Therapy Association, vol. 89, No. 2, Feb. 2009, 12 pages.
Ward et al., "Variation in Motor Theshold with Frequency Using kHz Frequency Alternating Current," Muscle and Nerve, Oct. 2001, 9 pages.
Webster's Third New International Dictionary of the English Language Unabridge, "Paresthesia," 1993, 3 pages.
Weinberg et al., "Increasing the oscillation frequency of strong magnetic fields above 101 kHz significantly raises peripheral nerve excitation thresholds," Medical Physics Letter, May 2012, 6 pages.
Wolter et al., "Continuous Versus Intermittent Spinal Cord Stimulation: An Analysis of Factors Influencing Clinical Efficacy," Neuromodulation: Technology at Neural Interface, www.neuromodulationjournal.com, 2011, 8 pages.
Woo MY, Campbell B. "Asynchronous Firing and Block of Peripheral Nerve Conduction by 20KC Alternating Current," Los Angeles Neuro Society, 1964, June 87-94, 5 pages.
Yearwood et al., "A Prospective Comparison of Spinal Cord Stimulation (SCS) Using Dorsal Column Stimulation (DCS), Intraspinal Nerve Root Stimulation (INRS), and Varying Pulse Width in the Treatment of Chronic Low Back Pain," Congress of Neurological Surgeons 56th Annual Meeting, Oct. 7-12, 2006, 2 pages.
Yearwood et al., "Pulse Width Programming in Spinal Cord Stimulation: A Clinical Study," Pain Physician Journal, Jul./Aug. 2010, 16 pages.
Yearwood et al., Case Reports: "A Prospective Comparison of Spinal Cord Stimulation (SCS) Using Dorsal Column Stimulation (DCS), Intraspinal Nerve Root Stimulation (INRS), and Varying Pulse Width in the Treatment of Chronic Low Back Pain," Presented at the Congress of Neurological Surgeons 56th Annual Meeting, Oct. 7-12, 2006, 7 pages.
Zhang et al., "Simulation Analysis of Conduction Block in Myelinated Axons Induced by High-Frequency Biphasic Rectangular Pulses," IEEE Transactions on Biomedical Engineering, vol. 53., No. 7, Jul. 2006, 4 pages.
Zhang et al., Changes Across Time in Spike Rate and Spike Amplitude of Auditory Nerve Fibers Stimulated by Electric Pulse Trains, Journal of the Association for Research of Otolaryngology, 2007, 17 pages.
Abejon et al., "Is Impedance a Parameter to be Taken into Account in Spinal Cord Stimulation?" Pain Physician, 2007, 8 pages.
Al-Kaisy et al., "Prospective, Randomized, Sham-Control, Double Blind, Crossover Trial of Subthreshold Spinal Cord Stimulation at Various Kilohertz Frequencies in Subjects Suffering from Failed Back Surgery Syndrome," International Neuromodulation Society, Jan. 2018, 9 pages.
Alo et al., "Factors Affecting Impedance of Percutaneous Leads in Spinal Cord Stimulation," International Neuromodulation Society, vol. 9, No. 2, 2006, 8 pages.
Bronstein et al., "The Rationale Driving the Evolution of Deep Brain Stimulation of Constant-Current Devices," International Neuromodulation Society 2014, 5 pages.
Burton, Charles, "Dorsal Column Stimulation: Optimization of Application," Surgical Neurology, vol. 4, No. 1, Jul. 1975, 10 pages.
Holsheimer—Effectiveness of Spinal Cord Stimulation in the Management of Chronic Pain: Analysis of Technical Drawbacks and Solutions, Neurosurgery, vol. 40, No. 5, May 1997, pp. 990-999.
McCreery et al., "Charge Density and Charge Per Phase as Cofactors in Neural Injury Induced by Electrical Stimulation," IEEE Transactions on Biomedical Engineering, vol. 37, No. 10, Oct. 1990, 6 pages.
McCreery et al., "Damage in Peripheral Nerve from Continuous Electrical Stimulation: Comparison of Two Stimulus Waveforms," Medical and Biological Engineering and Computing, Jan. 1992, 6 pages.
McCreery et al., "Relationship between Stimulus Amplitude, Stimulus Frequency and Neural Damage During Electrical Stimulation of Sciatic Nerve of a Cat," Medical and Biological Engineering and Computing, May 1995, 4 pages.
Nevro—Leadership Through Innovation, J. P. Morgan 36th Annual Healthcare Conference, Jan. 8, 2018, 21 pages.

(56) References Cited

OTHER PUBLICATIONS

Renew Neurostimulation System—Clinician's Manual—Advanced Neuromodulation Systems, Life Gets Better, 2000, 77 pages.

Rosenblueth et al., "The Blocking and Deblocking Effects of Alternating Currents on Nerve," Department of Physiology in Harvard Medical School, Nov. 1938, 13 pages.

St. Jude Medical, "Clinician's Manual—Percutaneous Lead Kit, Models 3143, 3146, 3149, 3153, 3156, 3159, 3183, 3186, 3189," 2016, 24 pages.

Thomson et al., "Effects of Rate on Analgesia in Kilohertz Frequency Spinal Cord Stimulation: Results of the PROCO Randomized Controlled Trial," Neuromodulation: Technology at the Neural Interface, 2017, 10 pages.

Wesselink et al., Analysis of Current Density and Related Parameters in Spinal Cord Stimulation, IEEE Transaction on Rehabilitation Engineering vol. 6, No. 2, Jun. 1998, 8 pages.

Kulkarni et al., "A two-layered forward model of tissue for electrical impedance tomography," Physiol Meas., 30(6); pp. 1-24, Jun. 2009.

Medtronic—Spinal Cord Stimulation (SCS) Patient Management Guidelines for Clinicians, 1999, 114 pages.

Siegel et al., "Prospective Randomized Feasibility Study Assessing the Effect of Cyclic Sacral Neuromodulation on Urinary Urge Incontinence in Women," Female Pelvic Med Reconstr Surg. 2018, 5 pages.

Cadish, "Stimulation Latency and Comparison of Cycling Regimens in Women Using Sacral Neuromodulation," Feb. 1, 2016, 4 pages.

\* cited by examiner

NEUROMODULATION FOR ALTERING AUTONOMIC FUNCTIONS, AND ASSOCIATED SYSTEMS AND METHODS

CROSS-REFERENCE TO RELATED APPLICATIONS

The present application claims priority to the following provisional applications, each of which is incorporated herein by reference: U.S. 62/246,514, filed Oct. 26, 2015; and U.S. 62/385,073, filed Sep. 8, 2016.

TECHNICAL FIELD

The present technology is directed generally to neuromodulation techniques for altering autonomic functions, and associated systems and methods.

BACKGROUND

Neurological stimulators have been developed to treat pain, movement disorders, functional disorders, spasticity, cancer, cardiac disorders, and various other medical conditions. Implantable neurological stimulation systems generally have an implantable pulse generator and one or more leads that deliver electrical pulses to neurological tissue or muscle tissue. For example, several neurological stimulation systems for spinal cord stimulation (SCS) have cylindrical leads that include a lead body with a circular cross-sectional shape and one or more conductive rings spaced apart from each other at the distal end of the lead body. The conductive rings operate as individual electrodes and, in many cases, the SCS leads are implanted percutaneously through a large needle inserted into the epidural space, with or without the assistance of a stylet.

While the foregoing stimulators and techniques have proven beneficial in many instances, there remains a significant need in the medical community for improved devices and therapies that can address a broad range of patient indications. In particular, there remains a need for addressing autonomic system dysfunctions.

DETAILED DESCRIPTION

1.0 Introduction

Figure 1:
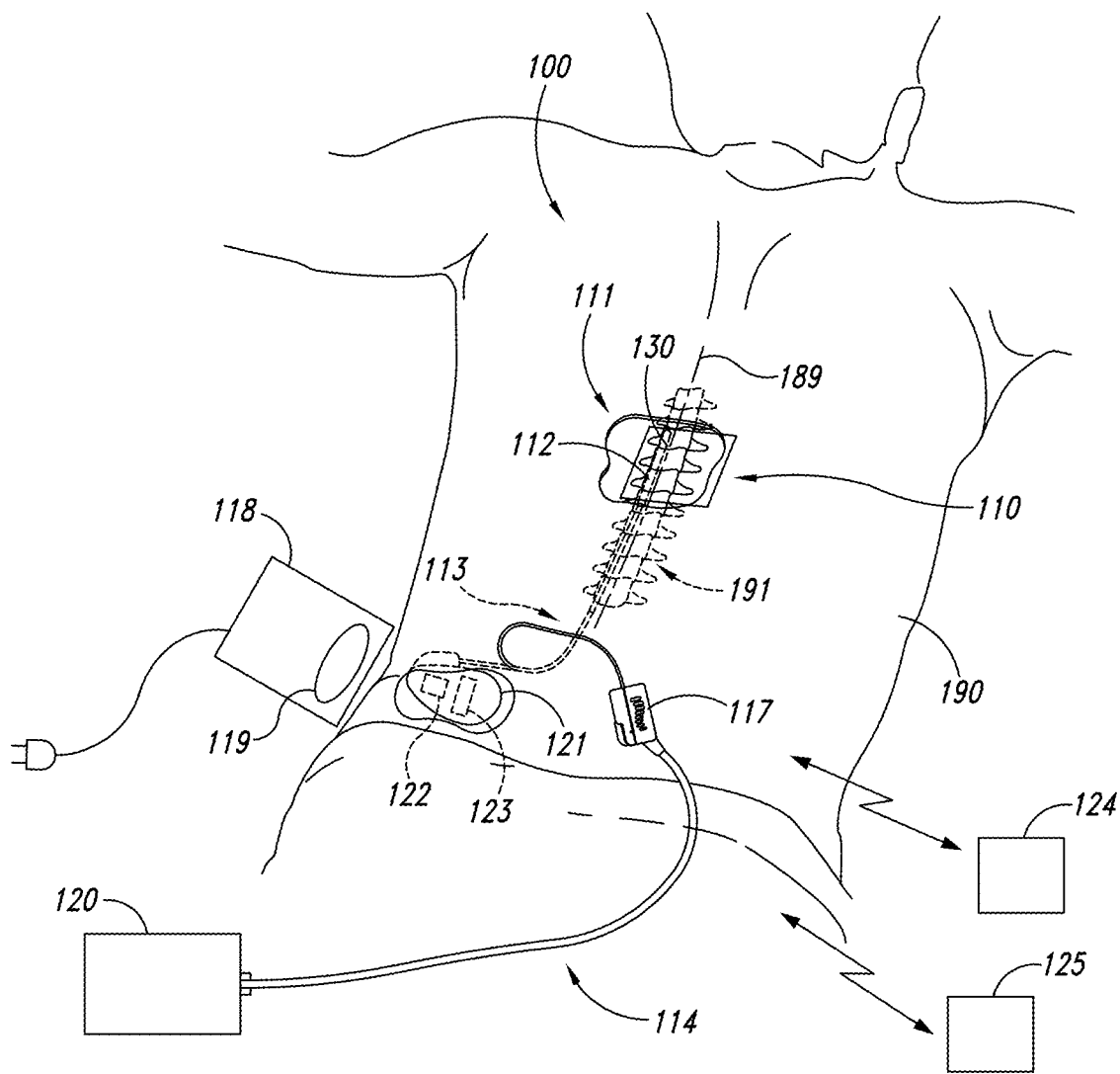
FIG. 1 is a partially schematic illustration of an implantable spinal cord modulation system positioned at the spine to deliver therapeutic signals in accordance with several embodiments of the present technology.

The present technology is directed generally to neuromodulation techniques for altering a patient's autonomic functions (e.g., signaling), and associated systems and methods. In particular embodiments, an electrical field is created via a therapeutic electrical signal delivered from a suitable signal delivery device positioned laterally in the ventral epidural space. Accordingly, the therapy can target a patient's ventral roots and ventral spinal cord structures. The position of the signal delivery device in the ventral epidural space is expected to modulate small autonomic, preganglionic fibers.

In other embodiments, the therapeutic signal can be applied from a signal delivery device having an extravertebral location, i.e., outside the foramen formed by the vertebrae of the spinal column. In this position, the signal delivery device can target sympathetic chain structures, for example, the sympathetic trunk, sympathetic ganglia, rami communicates, and/or sympathetic chain axons.

Whether the therapeutic signal is applied epidurally or extravertebrally, the signals are expected to modulate small fibers and/or ganglia to initiate therapeutic changes in the patient's autonomic function, in particular, inhibitory changes. Accordingly, as used herein, the terms "stimulate" and "stimulation" refer generally to signals, methods and/or systems that affect the functioning of the target neural population (e.g., in an excitatory or inhibitory way) via an electrical field. Representative functions include blood vessel diameter, blood pressure, cardiac function, kidney function, adrenal function, gastrointestinal function, autoimmune function (e.g., via splenic modulation) hepatic function, brain function, and/or pancreatic function.

2.0 The Autonomic Nervous System

The autonomic nervous system controls multiple organ systems in the body, and is required to maintain homeostasis. The autonomic nervous system includes two arms, branches, divisions or systems: the parasympathetic system and the sympathetic system. The parasympathetic system is generally active when the target or controlled organ is to be at rest. The sympathetic system is excitatory, and generally becomes active when the target organ system is to be aroused, for example, in response to an emergency. In a healthy patient, the two systems work in concert, with individual activities of daily living and external conditions to which the patient is subjected determining the relative balance of activity and inactivity between the sympathetic and parasympathetic systems.

When the patient is subjected to a disease, however, the two autonomic systems can be out of balance. One representative disease state is heart failure, during which the sympathetic output or tone is often chronically elevated. The activity level of the sympathetic system is elevated to compensate for the reduced function of a diseased heart (which can result, for example, from myocardial infarct, chronic coronary artery disease, and/or other conditions). During heart failure, the sympathetic system increases the resting heart rate and contractile force to improve cardiac output. The sympathetic system can also decrease the arterial vessel diameter to increase tissue perfusion. The increased excitatory drive produced by the sympathetic system has short-term benefits to the patient's bodily functions, but in the long term, can actually lead to increased symptoms, for example, ascites and/or fatigue. The increased excitatory drive can also accelerate chronic dysfunction of the cardiovascular system, for example, increasing the risk of arrhythmia and/or suppressing or eliminating the baroreflex. As a result, a typical first-line therapy for treating heart failure includes chronic oral beta blockers, to mitigate the increased release of circulating catecholamines, which may be triggered by the sympathetic nervous system.

One conventional therapeutic strategy for dealing with sympathetic system over-activity is to increase the output of the parasympathetic nervous system, which can operate to inhibit the sympathetic system. For example, one conventional treatment includes electrically stimulating the vagus nerve, which is the primary nervous system "pathway" that mediates parasympathetic tone. Vagus nerve stimulation (VNS) includes stimulation pulses having relatively low amplitudes that are delivered to the nerve to generate action potentials. The resulting action potential traffic on the nerves can then signal afferent destinations or efferent destinations of the nerves, and trigger further nervous system activities. For example, when VNS is used to treat heart failure, efferent vagal activity can direct signals to the vagus fat pads at the heart, which can slow the heart rate and thus counteract the effect of the sympathetic input to the heart.

One drawback with the foregoing VNS therapy approach is that it can be non-specific. For example, typical targets for VNS electrodes are at the large vagus branches in the neck, which carry parasympathetic afferent and efferent information to multiple organ systems of the body. As a result, VNS may have positive, intended effects at the heart, but because it is nonselective, may collaterally activate other vagal nerves that create undesirable side effects. Such side effects can include changes in gastrointestinal motility, motor activation of the laryngeal nerves (which can cause hoarseness or coughing), and/or other effects. Thus, while VNS can be valuable as a therapy for autonomic system imbalance, it does not adequately address the increased sympathetic tone in a targeted manner.

Other therapeutic techniques for addressing over-activity caused by the sympathetic system include dorsal epidural spinal cord stimulation (SCS). This approach is expected to more selectively alter the sympathetically-mediated disease symptoms. In particular embodiments, dorsal epidural SCS has been used to counteract the vasoconstriction observed in ischemic pain, (triggered, for example, by peripheral vascular disease, and/or angina) and/or complex regional pain syndrome. Dorsal epidural SCS strongly activates large myelinated dorsal afferents to drive inhibitory synapses in the intermediolateral column of the spinal cord, effectively reducing the sympathetic efferent output from the spinal cord. The result of this effect has been to increase blood flow in the periphery (due to reduced sympathetically-mediated small vessel vasoconstriction), as well as redistribute coronary artery flow. Because (unlike the main vagus nerves in the neck) the sympathetic nervous system efferents are widely distributed between vertebral levels T1-L2, the electrodes can be placed at different vertebral levels to more selectively affect different organ systems.

Nevertheless, dorsal epidural SCS typically requires relatively high stimulation amplitudes that in turn may yield uncomfortable or annoying paresthesias and/or muscle/motor affects. Accordingly, an alternative technique is to address the sympathetic efferents themselves directly by applying SCS to ventral (rather than dorsal) neural populations. Techniques for "blocking" nerve activity include direct current (DC) or depolarization blockade, which can be applied to the ventral roots of the spinal cord. However, these blocking techniques also include significant drawbacks. In particular, direct current (DC) stimulation is generally not used for neuromodulation in clinical settings because it leads to electrode corrosion and tissue damage. In addition, the signal amplitudes required for a depolarization blockade are much higher than for typical stimulation. If such high amplitude signals were applied to the ventral roots, then very large myelinated motor efferents would be strongly activated and blocked prior to activating (let alone blocking) the relatively small and lightly myelinated sympathetic efferent fibers. Put another way, if a blocking signal, having the high amplitude typical of such signals, were applied to the sympathetic efferent neural pathways, that signal would likely activate motor neurons (via efferent neural pathways), causing unwanted motor activity before creating the desired suppression of the sympathetic system.

Embodiments of the present technology are expected to address the foregoing drawbacks associated with conventional techniques by selecting target neural populations and/or signal delivery parameters in a manner that produces the desired inhibitory effect on the autonomic system, without creating unwanted side effects.

Several aspects of the technology are embodied in special-purpose computing devices, e.g., programmed/programmable pulse generators, controllers and/or other devices. The computing devices on which the described technology can be implemented may include one or more central processing units, memory, input devices (e.g., input ports), output devices (e.g., display devices), storage devices, and network devices (e.g., network interfaces) that are specially configured to perform the methods described herein. The memory and storage devices are computer-readable media that may store instructions that implement the technology. In many embodiments, the computer-readable media are tangible media. In other embodiments, the data structures and message structures may be stored or transmitted via an intangible data transmission medium, such as a signal on a communications link. Various suitable communications links may be used, including but not limited to a local area network and/or a wide-area network.

3.0 Overall System Characteristics

FIG. 1 schematically illustrates a representative patient system 100 for altering the function, balance, and/or other attributes of the autonomic system, arranged relative to the general anatomy of a patient's spinal cord 191. The overall patient system 100 can include a signal delivery system 110, which may be implanted within a patient 190, typically offset from the patient's midline 189, and coupled to a pulse generator 121. The signal delivery system 110 can provide therapeutic electrical signals to the patient during operation. In a representative example, the signal delivery system 110 includes a signal delivery device 111 that carries features for delivering therapy to the patient 190 after implantation. The pulse generator 121 can be connected directly to the signal delivery device 111, or it can be coupled to the signal delivery device 111 via a signal link (e.g., a hardwired extension cable 113, or wireless signal transmitter (not shown)). In a further representative embodiment, the signal delivery device 111 can include an elongated lead or lead body 112. As used herein, the terms "lead" and "lead body" include any of a number of suitable substrates and/or support members that carry devices for providing therapy signals to the patient 190. For example, the lead 112 can include one or more electrodes or electrical contacts that direct electrical signals into the patient's tissue, for example, to modulate the patient's autonomic system. In other embodiments, the signal delivery device 111 can include structures other than a lead body (e.g., a paddle) that also direct electrical signals and/or other types of signals to the patient 190.

The pulse generator 121 can transmit signals (e.g., electrical signals) to the signal delivery device 111 that increase (e.g., stimulate or excite) and/or decrease (e.g., block, inhibit, or suppress) activity in target nerves. As used herein, and unless otherwise noted, the terms "modulate" and "modulation" refer generally to signals that have either type of the foregoing effects on the target nerves. The pulse generator 121 can include a machine-readable (e.g., computer-readable) medium containing instructions for generating and transmitting suitable therapy signals. The pulse generator 121 and/or other elements of the system 100 can include one or more special-purpose processors 122, memories 123 and/or input/output devices. Accordingly, the process of providing modulation signals, providing guidance information for locating the signal delivery device 111, and/or executing other associated functions can be performed by computer-executable instructions contained by computer-readable media located at the pulse generator 121 and/or other system components. The pulse generator 121 can include multiple portions, elements, and/or subsystems (e.g., for directing signals in accordance with multiple signal delivery parameters), carried in a single housing, as shown in FIG. 1, or in multiple housings.

In some embodiments, the pulse generator 121 can obtain power to generate the therapy signals from an external power source 118. The external power source 118 can transmit power to the implanted pulse generator 121 using electromagnetic induction (e.g., RF signals). For example, the external power source 118 can include an external coil 119 that communicates with a corresponding internal coil (not shown) within the implantable pulse generator 121. The external power source 118 can be portable for ease of use.

The pulse generator 121 can be implanted above the patient's buttock in an embodiment shown in FIG. 1, or at other locations in other embodiments. Other suitable locations include sub-clavicular locations, or locations along the neck (e.g., when the pulse generator includes a microstimulator or other suitably small device).

In at least one embodiment, an external programmer 120 (e.g., a trial modulator) may be coupled to the signal delivery device 111 during an initial "trial" procedure, prior to permanently implanting the pulse generator 121. For example, a practitioner (e.g., a physician and/or a company representative) can use the external programmer 120 to provide the therapy signal to the signal delivery device 111, vary the modulation parameters in real time, and select optimal or particularly efficacious parameters. These parameters can include the location from which the electrical signals are emitted, as well as the characteristics of the electrical signals provided to the signal delivery device 111. In a typical process, the practitioner uses a cable assembly 114 to temporarily connect the external programmer 120 to the signal delivery device 111. The practitioner can test the efficacy of the signal delivery device 111 in an initial position. The practitioner can then disconnect the cable assembly 114 (e.g., at a connector 117), reposition the signal delivery device 111, and reapply the electrical modulation. This process can be performed iteratively until the practitioner obtains the desired position for the signal delivery device 111. Optionally, the practitioner may move the partially implanted signal delivery element 111 without disconnecting the cable assembly 114. In still further embodiments, the foregoing iterative process can be eliminated, for example, because the characteristics of the signal and/or the ability to direct the signal from any of a plurality of electrodes eliminate the need to move the signal delivery device 111 during the trial period.

After a trial period with the external programmer 120, the practitioner can permanently implant the implantable pulse generator 121 within the patient 190 for longer term treatment. The signal delivery parameters provided by the pulse generator 121 can still be updated after the pulse generator 121 is implanted, via a wireless physician's programmer 125 (e.g., a physician's remote) and/or a wireless patient programmer 124 (e.g., a patient remote). Generally, the patient 190 has control over fewer parameters than does the practitioner.

4.0 Target Neural Populations and Lead Locations

Figure 2:
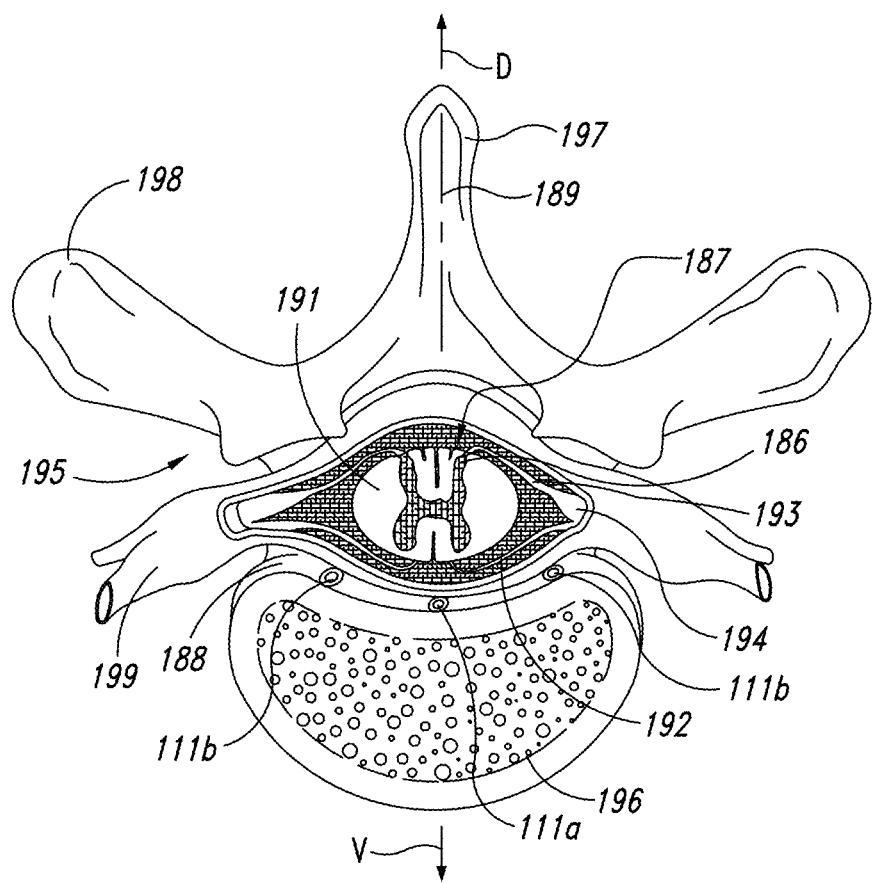
FIG. 2 is a partially schematic, cross-sectional illustration of a patient's spine, illustrating representative locations for implanted lead bodies in accordance with embodiments of the present technology.

FIG. 2 is a cross-sectional illustration of the spinal cord 191 and an adjacent vertebra 195 (based generally on information from Crossman and Neary, "Neuroanatomy," 1995 (published by Churchill Livingstone)), along with multiple signal delivery devices 111 (shown as signal delivery devices 111a-111b) implanted at representative locations. For purposes of illustration, multiple signal delivery devices 111 are shown in FIG. 2 implanted in a single patient. In actual use, any given patient may receive fewer than all the signal delivery devices 111 shown in FIG. 2.

The spinal cord 191 is situated within a vertebral foramen 188, between a ventrally located ventral body 196 and a dorsally located transverse process 198 and spinous process 197. Arrows V and D identify the ventral and dorsal directions, respectively. The spinal cord 191 itself is located within the dura mater 199, which also surrounds portions of the nerves exiting the spinal cord 191, including the ventral roots 192, dorsal roots 193 and dorsal root ganglia 194. The dorsal roots 193 enter the spinal cord 191 at the dorsal root entry zone 187, and communicate with dorsal horn neurons located at the dorsal horn 186.

In one embodiment, a single first signal delivery device 111a is positioned at a ventral location within the vertebral foramen 188 (e.g., within the patient's spinal canal), at or approximately at the spinal cord midline 189. Similarly, in another embodiment, one or more signal delivery devices 111b are positioned off the spinal cord midline 189, laterally or bilaterally. From these locations, the signal delivery device(s) 111 can direct therapeutic signals to ventral neural populations at the spinal cord 191 itself, or to neural populations in the region of the spinal cord, but off the spinal cord itself, e.g., the laterally-positioned ventral roots 192.

In general, the signal delivery device(s) 111 (and more particularly, the electrodes carried by the signal delivery device(s) 111) are positioned proximate to (e.g., within 0.5 mm-10 mm of) the target neural population. The specific location within the foregoing range can be selected by the practitioner to produce the desired therapeutic outcome without generating collateral effects (e.g., without adversely affecting nearby neural structures). In still further embodiments, one or more signal delivery devices can be positioned laterally or bilaterally at other locations. Representative locations are described further below with reference to FIGS. 3-6B.

FIGS. 3-6B are adapted from corresponding figures available online at http://humanphysiology.academy/Neurosciences %202015/Chapter %202/A.2.1%20Spinal %20Cord.htm. These Figures illustrate representative target neural tissues that receive electrical signals in accordance with embodiments of the present technology. In many instances, the target tissues include neural populations, e.g., neurons. In other embodiments, other tissues, in addition to or in lieu of neural tissue, can respond to the electrical signals and produce therapeutic results. Examples of other suitable tissues include glial cells, blood cells, plasma, lymphatic tissue, fat, meninges, bone, muscle, vasculature, endothelial tissue, endoneurial tissue, and epineurial tissue.

Figure 3:
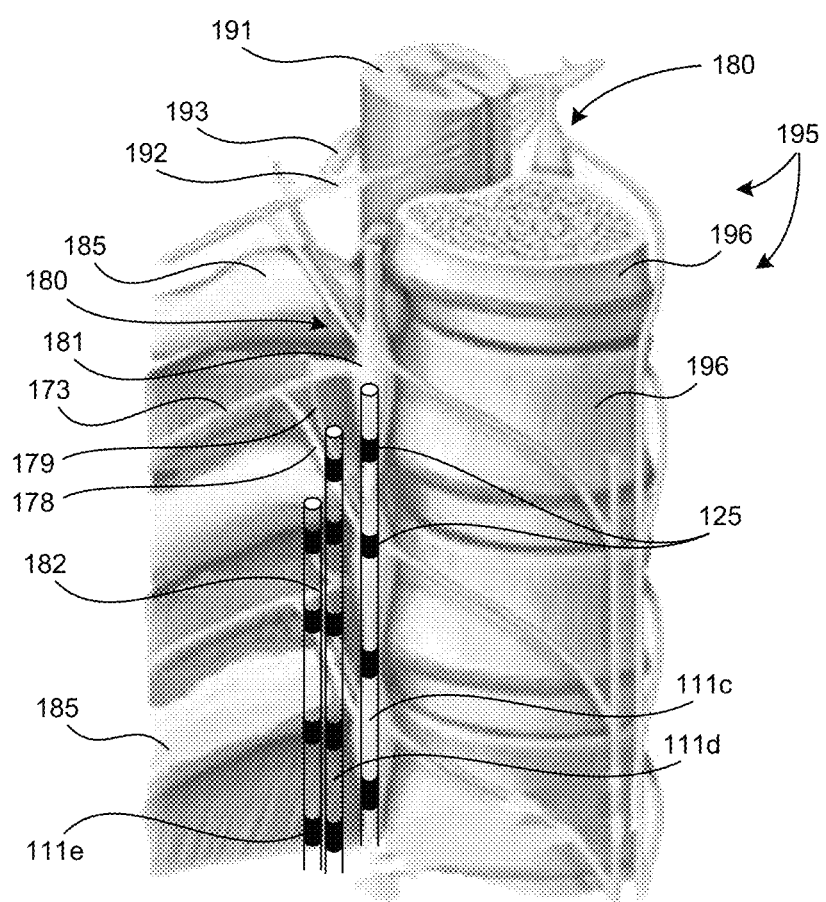
FIG. 3 is a partially schematic isometric illustration of a portion of a patient's spine, spinal cord, and sympathetic trunk, illustrating leads positioned extravertebrally in accordance with embodiments of the present technology.

FIG. 3 a partially schematic, isometric illustration of a portion of the patient's spinal column, including the ventral bodies 196 of multiple corresponding vertebrae 195. FIG. 3 also illustrates the spinal cord 191 (which is positioned dorsally from the ventral bodies 196) and associated ribs 185. Bilateral sympathetic trunks or chains 180 are positioned outside the spinal column. Each sympathetic trunk 180 includes sympathetic trunk ganglia 181. Spinal nerves 173 connect to the sympathetic trunk ganglia 181 via a ventral ramus 182, gray ramus communicans 179, and white ramus communicans 178. The discussion below is focused on the right-side neural structures (which are more visible in the Figures) and applies equally to the patient's left-side neural structures.

Representative signal delivery devices can be positioned outside the spinal column (e.g., outside the spinal canal) to generate an electrical field at target neural populations of the sympathetic system shown in FIG. 3. For example, a representative signal delivery device 111c is shown positioned along the sympathetic trunk 180 to direct electrical signals to one or more sympathetic trunk ganglia 181. Other representative signal delivery devices 111d, 111e are positioned laterally outwardly from the sympathetic trunk 180 to direct electrical signals to the ventral ramus 182, gray ramus communicans 179, and/or white ramus communicans 178. Each signal delivery device 111c, 111d, 111e can include one or more electrodes 125 to deliver a therapeutic signal to one or more target neural populations. As discussed above with reference to FIG. 2, multiple signal delivery devices are shown together in FIG. 3 for purposes of illustration. While patients may receive multiple implanted devices, representative implantation arrangements include a single unilaterally positioned signal delivery device, or two signal delivery devices positioned in a symmetric, bilateral configuration. In other embodiments, patients may receive multiple unilaterally positioned signal delivery devices, and/or multiple pairs of bilaterally positioned signal delivery devices, which need not be positioned symmetrically.

Figure 4:
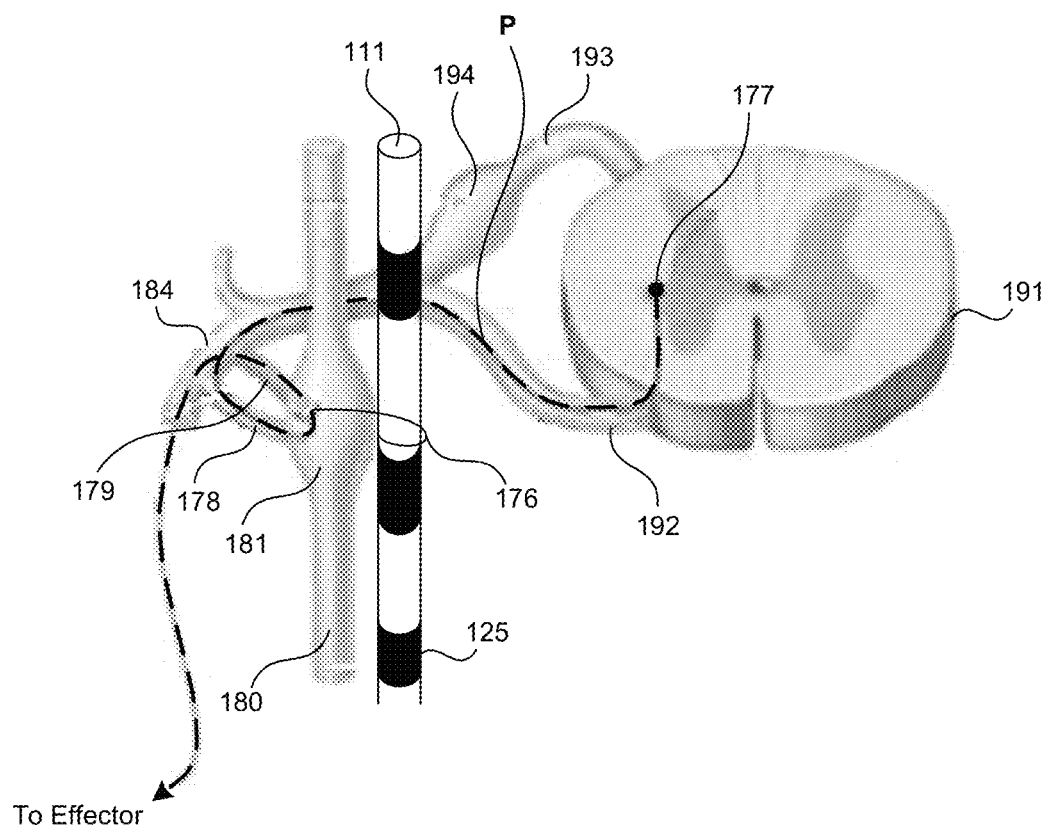
FIG. 4 is a partially schematic illustration a portion of a patient's spinal cord, including a ventral root and a sympathetic trunk synapse at approximately the same vertebral level, with a signal delivery device positioned to provide an electrical signal in accordance with an embodiment of the present technology.

FIG. 4 is an enlarged view of a portion of the patient's spinal cord 191 illustrating the dorsal root 193 and the ventral root 192. The internal structure of the spinal cord includes a lateral horn 177 from which visceral motor efferents originate as indicated in dotted lines by an efferent signal path P. The efferent signal path P passes to a sympathetic trunk ganglion 181 of the sympathetic trunk 180, via the white ramus communicans 178, and then to the ventral ramus of the spinal nerve 184 via the gray ramus communicans 179. A representative signal delivery device 111 is shown positioned along the sympathetic trunk 180 to provide electrical signals to the sympathetic trunk ganglion 181. In other embodiments, for example, as discussed above with reference to FIG. 3, the signal delivery device 111 can be positioned laterally outwardly from the location shown in FIG. 4 to direct signals to the ventral ramus 184, gray ramus communicans 179 and/or white ramus communicans 178. In other embodiments, in addition to, or instead of relying upon physical positioning of the stimulation delivery devices, stimulation parameters may be selected to provide stimulation to more than one particular neural structure for a given electrode position. For example, in FIG. 4, to selectively target the sympathetic trunk ganglion 181, the contact most adjacent to the ganglion may be activated and a low amplitude electrical field utilized. Alternatively, to affect both the ganglion 181 and the sympathetic trunk 180, multiple contacts may be activated, with a relatively higher stimulation amplitude.

Figure 5:
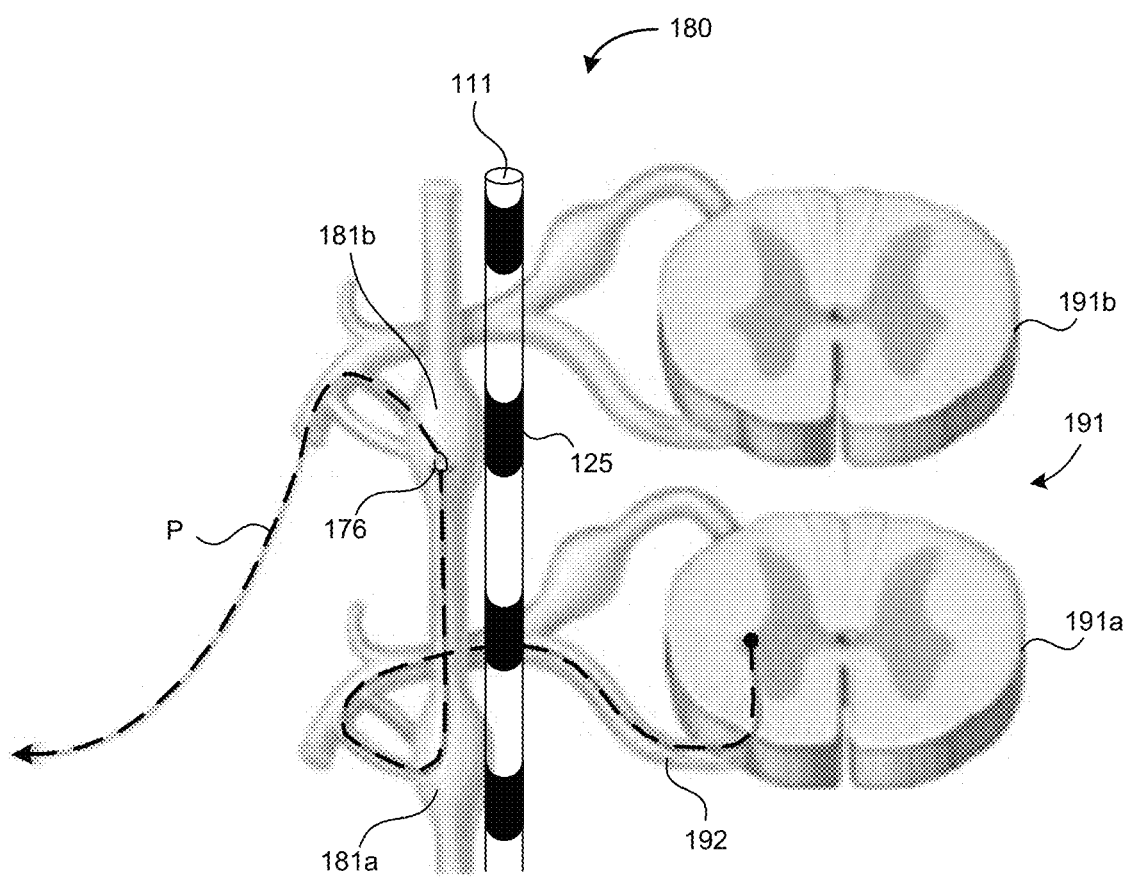
FIG. 5 is a partially schematic illustration of two sections of a patient's spinal cord at different vertebral levels, with a sympathetic trunk synapse at a different vertebral level than a corresponding ventral root, and with a signal delivery device positioned to provide an electrical signal in accordance with an embodiment of the present technology.

As shown in FIG. 4, the efferent path P passes through a synapse 176 at the sympathetic trunk ganglion 181. The synapse 176 is located at approximately the same vertebral level as the portion of the lateral horn 177 from which the efferent signal path P emanates. As shown in FIG. 5, the synapse 176 can have other locations. In particular, FIG. 5 illustrates two portions of the patient's spinal cord 191, shown as a first portion 191a, located at a first vertebral level, and a second portion 191b, located at a second vertebral level. The sympathetic trunk 180 includes corresponding first and second ganglia 181a, 181b located at approximately the same vertebral levels as the first and second spinal cord sections 191a, 191b, respectively. As shown in FIG. 5, the efferent signal path P emanating from the first spinal cord section 191a synapses not at the first ganglion 181a, but at the second ganglion 181b. Accordingly, the practitioner can position the signal delivery device 111 to activate one or more electrodes 125 at the second sympathetic trunk ganglion 181b. More generally, the practitioner can activate electrodes 125 at one or more of multiple sympathetic trunk ganglia 181 so as to address synapses that are at the same or a different vertebral level than the origination of the efferent signal path P. The signal delivery device 111 can accordingly include multiple electrodes 125 to provide the practitioner with enough flexibility to target any of a suitable plurality of target neural populations. Further details of representative signal delivery devices are described later with reference to FIG. 7.

In still further embodiments, the practitioner can target other ganglia. For example, referring now to FIG. 6A, the efferent signal path P can include a synapse 176 at a prevertebral or collateral ganglion 175, which communicates with the sympathetic trunk 180 and associated sympathetic trunk ganglion 181 via a splanchnic nerve 174. The associated signal delivery device 111 can be positioned so that one or more electrodes 125 are located to direct electrical signals to the collateral ganglion 175.

Figure 6A:
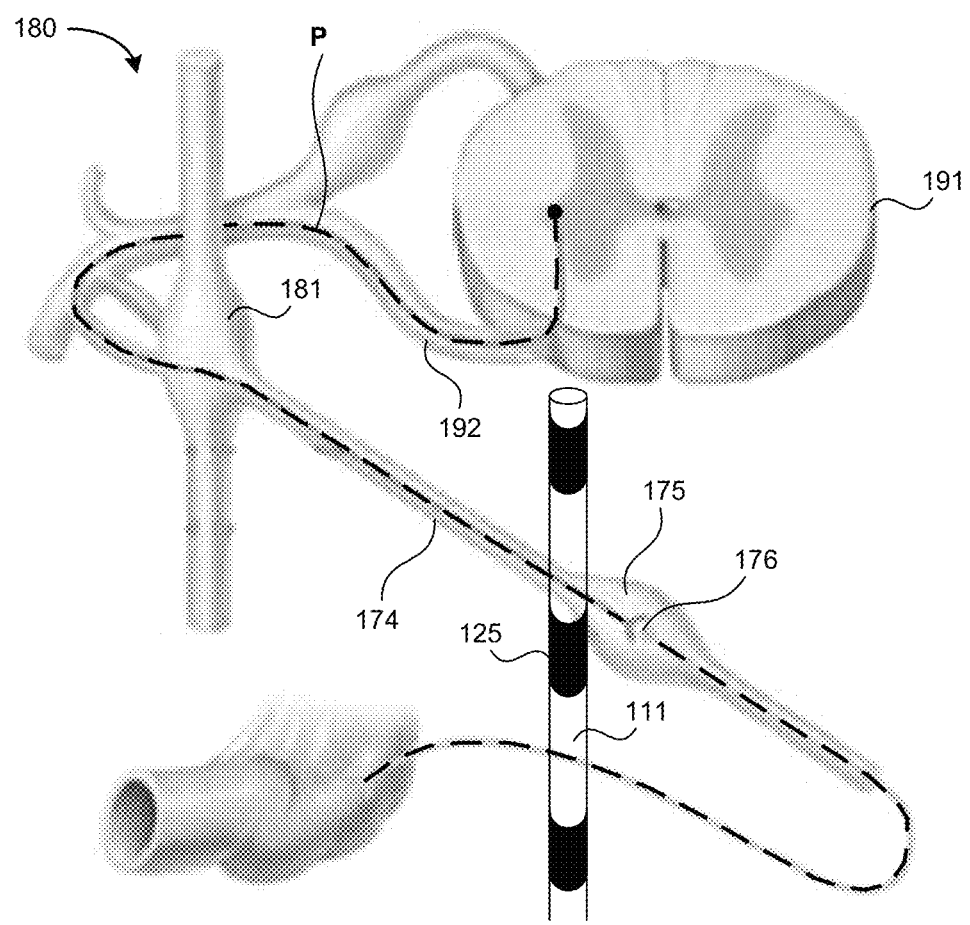
FIG. 6A is a partially schematic illustration of a portion of a patient's spinal cord, and a signal delivery device positioned proximate to a collateral ganglion in accordance with an embodiment of the present technology.

In general, it may be preferable to stimulate the sympathetic system at locations closer to the spinal column (as shown in FIGS. 3-5), rather than those more distant from the spinal column (as shown in FIG. 6A). In particular, the collateral ganglion 175 (e.g., the celiac ganglion) is located very near to the patient's aorta. Accordingly, the practitioner may prefer to avoid locating a signal delivery device at this location. Furthermore, the practitioner may prefer to provide stimulation extravertebrally, as shown in FIGS. 3-6B rather than epidurally, as shown in FIG. 2, because it is expected that the extravertebral (and extradural) stimulation will be even more selective and therefore less likely to have potentially undesirable side-effects on other neural structures. On the other hand, the neural targets are not expected to be as well-defined extradurally as they are epidurally. In addition, it may be more difficult to anchor electrodes extradurally than epidurally. Still further, there may be a larger pool of practitioners who have experience with epidural lead placement than with extradural lead placement. Accordingly, the practitioner may prefer the epidural location. The practitioner can, of course, weigh the foregoing factors (and others), together with the possibility of collaterally stimulating motor fibers or vascular structures in the ventral space when the signal delivery device is placed epidurally, so as to select a suitable signal delivery site.

As described above, the practitioner can locate the signal delivery device(s) at a variety of lateral locations to modulate a corresponding variety of target neural populations. The practitioner can also select a location along the rostral/caudal (longitudinal) axis to target effector signal paths for selected organs. Table 1 below outlines generally the target organs and associated vertebral levels for modulating autonomic activity in the manner described above.

TABLE 1

| Target Organ | Vertebral Level |
|---|---|
| Brain/Meninges | T1-T2 |
| Stomach | T6-T10 |
| Eye | T1-T2 |
| Cardiac | C6-C7, T1-T5 |
| Face/Neck/Ears-Nose-Throat Glands | T2-T4 |
| Larynx/Trachea/Bronchi | T1-T4 |
| Lungs | T2-T7 |
| Duodenum | T5-T10 |
| Pancreas | T8-T9 |
| Jejunum and Ileum | T5-T9 |
| Small Intestine | T9-T11 |
| Large Intestine | T5-T11 |
| Colon | T10-L3 |
| Spleen | T6-T8 |
| Gall Bladder/Liver | T6-T9 |
| Kidneys | T11-T12 |
| Ureters | L1-L2, S2-S4 |
| Adrenal Gland | T11-L1 |
| Target Organ | Vertebral Level |
| Upper Extremity Vasomotor | T5-T7 |
| Lower Extremity Vasomotor | T10-L2 |

In particular examples, therapeutic signals are directed to neural targets of the patient to address cardiac functioning. For example, electrical therapy signals can be applied to the stellate sympathetic ganglia, superior cervical ganglia, inferior cervical ganglia, and/or upper thoracic (e.g., T1-T4) sympathetic ganglia (hereafter referred to as cardiovascular ganglia) to affect cardiovascular parameters. Such cardiovascular parameters can include: cardiac rate and/or conduction metrics (Purkinje conduction time within the atrioventricular [AV] node, bundle of His conduction time, atrial and ventricular Purkinje network conduction time, PR interval, cardiac myocyte action potential duration, QT interval, ST segment elevation, T-wave duration, cardiac myocyte refractory time, and/or cardiac myocyte population refractory dispersion) and/or blood pressure metrics (mean blood pressure, contractility [dP/dt], systolic blood pressure, diastolic blood pressure, and/or pulse pressure).

In a particular embodiment, the amplitude and/or frequency of the signal applied to the cardiovascular ganglia may be adjusted to affect a particular cardiovascular parameter, e.g., heart rate and/or blood pressure, for a given state of the patient. A representative algorithm identifies an amplitude of the signal (at a fixed frequency) that achieves a target heart rate and/or blood pressure, with the patient in a resting state and under a stable pharmacologic regimen. In another embodiment, the signal amplitude may be fixed while the frequency is altered to achieve a target heart rate and/or blood pressure. Heart rate and/or blood pressure reduction can occur in a dose-dependent fashion. For example, at an effective stimulation amplitude, as frequency is increased between 1 kHz and 15 kHz, the heart rate and/or blood pressure are expected to decrease by increasing amounts. Alternatively, at a fixed frequency, as stimulation amplitude is increased above a nominal threshold (e.g., starting from a value in the range of 2 mA-15 mA), cardiovascular parameters such as heart rate and/or blood pressure are expected to be progressively reduced.

The therapy signal can be applied in a closed-loop manner. For example, a practitioner can identify a target heart rate range for a patient, and the patient's EKG can be measured using electrodes connected to the stimulation and measurement system (e.g., the pulse generator), and implanted within the patient's body. This arrangement can provide feedback which is used to update the therapy signal parameters. In a particular embodiment, the therapy signal amplitude is varied depending upon the measured heart rate. For example, the delivery parameters of the therapy signal may not change until the heart rate exceeds a predefined threshold, and are adjusted in a direction that returns the heart rate to within a previously-programmed or otherwise identified range.

The high frequency signal can be applied to the cardiovascular ganglia to reduce the likelihood of arrhythmia. For example, the signal can be applied (or applied at an increased intensity, if already active) when the system senses ectopic episodes. Such episodes can include premature ventricular contractions or PVC, runs of ventricular or atrial tachycardia, and/or other arrhythmic EKG patterns. In this embodiment, the signal parameters are maintained as needed until normal sinus rhythm is reestablished for a pre-programmed period of time after the last pro-arrhythmic event is detected (e.g., 10 minutes after the last detected PVC). In this manner, the therapy signal applied to the cardiovascular ganglia can reduce the likelihood of an onset of pathologic, morbid, and/or fatal arrhythmias.

In another embodiment, the therapy signal can be used to abort ongoing arrhythmias. When an arrhythmia is detected (e.g., via an EKG sensor), the therapy signal frequency and/or amplitude may be stepwise increased up to pre-programmed limits to progressively eliminate the level of sympathetic tone that may be enabling the arrhythmia. The therapy signal can be applied as long as the arrhythmia is present and, as discussed above, can be maintained for some time after the arrhythmia has ended to increase the likelihood that the heart rate will remain stable.

In another embodiment, hypertension can be treated by applying a high frequency, generally low intensity therapy signal to the cardiovascular ganglia. In a representative example, the practitioner establishes a target blood pressure range for the patient, and uses a blood pressure sensor (e.g., a piezoelectric transducer in or near a major artery) or surrogate (e.g., an optical pulse plethysmograph positioned near arterioles and/or capillaries). The amplitude and/or frequency of the therapy signal can be adjusted in a closed-loop fashion to maintain the blood pressure within a pre-determined range.

In yet another embodiment, the therapy signal can be adjusted in response to input from a sensor that measures activity level, posture and/or physiologic metrics (e.g., blood oxygen saturation, minute ventilation, and/or cardiac contractility via dP/dt). Accordingly, the system can vary the signal delivery parameters with patient activity or physiologic need in a more sophisticated manner, as this physiologic measure may be used alone or in concert with the measured heart rate to determine the delivery parameters of the therapy signal. For example, if the heart rate begins to decrease to slightly below a previously programmed (or otherwise identified) lower bound, but the pulse pressure has increased, the therapy signal parameters may not be adjusted because the net cardiac output is likely similar despite the lower heart rate. However, if both the heart rate and the pulse pressure were to increase above pre-determined bounds, then the strength of the therapy signal may be increased to produce a decrease in sympathetic drive to the heart and/or arterial vasculature.

In particular embodiments, low intensity electrical stimulation at high frequencies is coupled with high intensity electrical stimulation at low frequencies (e.g., from 1 Hz to less than 1000 Hz) to bi-directionally affect post-synaptic sympathetic ganglion cells. Accordingly, the high frequency signal can reduce output activity and the low frequency signal can increase neuron output activity.

In a particular embodiment, the two forms of stimulation (high frequency and low frequency) may be applied bilaterally to left and right sympathetic ganglion, respectively. This may allow the practitioner to more selectively tune particular cardiovascular variables. For example, it has been observed that pharmacologically blocking the right stellate ganglia tends to reduce heart rate and blood pressure while pharmacologically blocking the left stellate ganglia will reduce blood pressure. Thus, to selectively alter the heart rate with minimal effect on blood pressure, the practitioner can apply high frequency, low intensity stimulation to the right stellate ganglion for an inhibitory effect on sympathetic output, while providing low frequency, high intensity stimulation to the left stellate ganglion for promoting/increasing sympathetic output. The net effect may reduce heart rate while reducing (e.g., minimizing) the effect of the stimulation on blood pressure.

Signal delivery devices of the type described above with reference to FIGS. 1 and 2, and below with reference to FIG. 7, may be used to direct the therapy signal to the target site. In other embodiments, one or more microstimulators (e.g., with one or more electrical contacts per microstimulator) may be placed such that the middle/central contacts along the microstimulator are aligned with the center part of the ganglion. Each microstimulator may contain its own power source or may be externally powered via radiofrequency energy. Each microstimulator may be individually addressable or all may respond identically to an external field. The microstimulator(s) can include integral contacts, or can be coupled to a lead that carries the contacts.

Figure 6B:
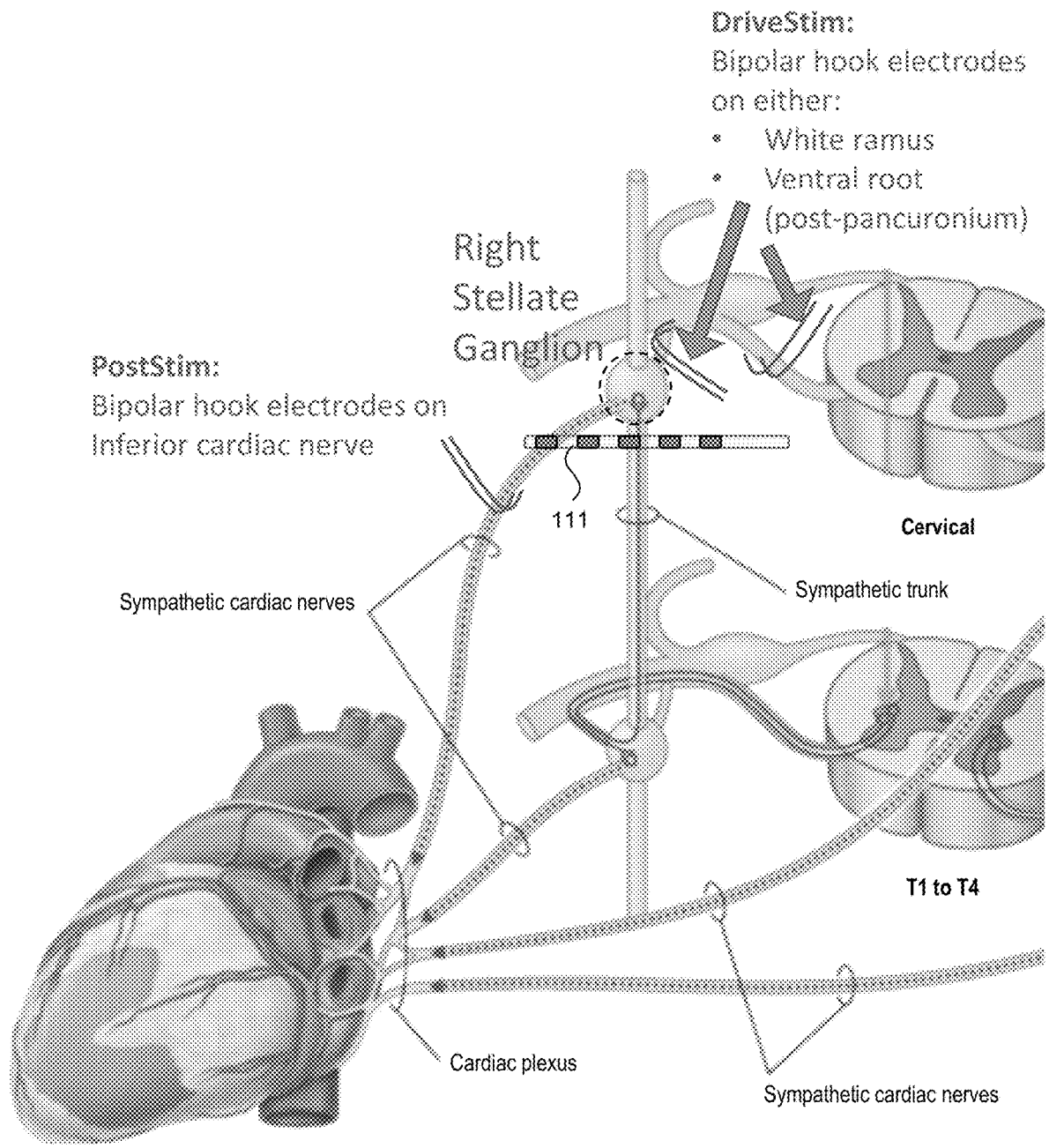
FIG. 6B is a partially schematic illustration of a portion of a patient's spinal cord, and a signal delivery device positioned proximate to a stellate ganglion in accordance with an embodiment of the present technology.

FIG. 6B illustrates a representative signal delivery device 111 positioned adjacent to the right stellate ganglion of a patient to produce any of the foregoing cardiac effects. In a representative experimental setting (e.g., possibly used intraoperatively for a given patient, prior to implant to determine possible effectiveness of the therapy as well as a range of effective thresholds), the efficacy of the stimulation applied to the right stellate ganglion can be evaluated with a series of additional temporary electrodes (shown schematically in FIG. 6B). In a representative experimental setting, one or more temporary electrodes (identified as "DriveStim" in FIG. 6B) are placed on the white ramus or the ventral root to supply an excitatory signal to the right stellate ganglion. One or more temporary electrodes (identified as "PostStim" in FIG. 6B) can be placed on an inferior cardiac nerve, between the heart and the right stellate ganglion to apply further test signals. In a representative experiment, the "DriveStim" electrodes can be activated to direct an excitatory signal to the right stellate ganglion, and the signal delivery device 111 can be activated to inhibit or prevent output from the right stellate ganglion in response to the excitatory signals. The "PostStim" electrodes can be activated to demonstrate that the sympathetic cardiac nerves remain viable despite the temporary inhibition provided by the signal delivery device 111. The efficacy of the signal delivery device can be determined by measuring any of the cardiac parameters described above, for example, heart rate and/or blood pressure. In this particular 'test screening,' if a patient's heart rate is first elevated by the 'DriveStim,' then reduced by the high frequency stimulation applied to the right stellate ganglion, then increased again by the 'PostStim,' the patient might pass the test screening and receive a permanent implant of the electrodes positioned near the right stellate ganglion. These electrodes would be atraumatically anchored so that their proximity to the right stellate ganglia is maintained. Additionally, the range of amplitudes needed to reduce the heart rate would be noted and placed in memory of the stimulation system. These could be recalled in a later clinic follow-up to provide a starting point for more optimal programming after recovery from implant surgery in a clinical setting.

5.0 Representative Signal Delivery Parameters

In any of the foregoing embodiments, the signal applied to the patient's target neural population is pulsed. Accordingly, the signal has, associated with it, a frequency, pulse width and amplitude. In representative embodiments, the frequency of the signal can range from 1 Hz to 100,000 Hz (i.e., 100 kHz), with frequencies between 1 Hz and less than 1000 Hz generally used for neuronal activation, and frequencies between 1000 Hz and 100,000 Hz generally used for neuronal inhibition. In more particular embodiments, the frequency ranges from 1 kHz to 100 kHz, from 1 kHz to 50 kHz, from 1 kHz to 20 kHz, from 1 kHz to 15 kHz, from 1 kHz to 10 kHz, from 1.5 kHz to 15 kHz, from 1.5 kHz to 10 kHz, from 2 kHz to 20 kHz, from 3 kHz to 10 kHz, from 5 kHz to 10 kHz, or from 9 kHz to 12 kHz. The pulse width can range from 1 microsecond to 1,000 microseconds and, in a particular embodiments, from 10 to 333 microseconds, from 10 to 250 microseconds, from 10 to 166 microseconds, from 10 to 100 microseconds, from 10 to 50 microseconds, or from 10 to 30 microseconds.

The signal amplitude can be selected to provide effective therapeutic results, without overstimulating the patient and/or otherwise generating or inducing accompanying side effects. In general, the amplitude of the signal can be inversely correlated with the pulse width of the signal, so as to prevent the therapy from depositing too large an electrical charge with a given pulse. Typical amplitudes will be dependent upon the proximity of the electrical contacts to the ganglion, the size of the contacts, and/or the separation distance between neighboring contacts. In a representative embodiment, the signal amplitude is programmable from 0-12V and/or 0-25 mA, with a range of 0.1V-3V and/or 0.1 mA-4 mA in a particular embodiment. The range of programmable pulse widths can depend upon the particular frequency applied, and can vary from 1 μsec.-1000 μsec., with a range of 5 μsec.-50 μsec. in a particular embodiment. The signal waveform can be a symmetric biphasic pulse waveform, which can be square, sinusoidal, or triangular. In further particular embodiments, the signal amplitude is expected to be less than 15 milliamps, or from 0.01 milliamp to five milliamps, or from 0.05 milliamp to 1 milliamp, or less than one milliamp, depending upon the embodiment, whether the signal is applied epidurally or extradurally. At such amplitudes, the signal is expected to be subthreshold to both motor and sensory neurons. Accordingly, the signal is not expected to produce detectable or noticeable action potentials in either sensory or motor neural populations. As a result, the patient is not expected to experience any sensory discomfort (e.g., shocking, tingling, numbness, paresthesia, or other sensations) and is also not expected to experience unwanted motor effects (e.g. twitching, jerking, tetany, or other effects). It is possible that, in at least some embodiments, the applied therapy signal will generate one or more action potentials. However, it is expected that in such cases, the ratio of stimulation pulses that generate an action potential to stimulation pulses that do not generate an action potential is less than 1:100. At this action potential generation rate, even though an occasional action potential is generated, it is not expected to be sufficient for the patient to sense it, nor sufficient to trigger a sensory or motor response.

Another signal delivery parameter associated with the foregoing therapy is the length of time over which the signal is delivered. For example, the therapy may be applied for a period of time as short as five minutes, to a period of time as long as multiple weeks without interruption (except for charging the device in the case of a functionally depleted battery). In a particular embodiment, the therapy is applied for approximately 30 minutes continuously, one time per day. In another representative embodiment, the signal is applied for a period of 10 minutes per day. In general, it is expected that the signal will be delivered either continuously or once per day to maintain the efficacy of the therapy.

6.0 Signal Delivery Devices

Figure 7:
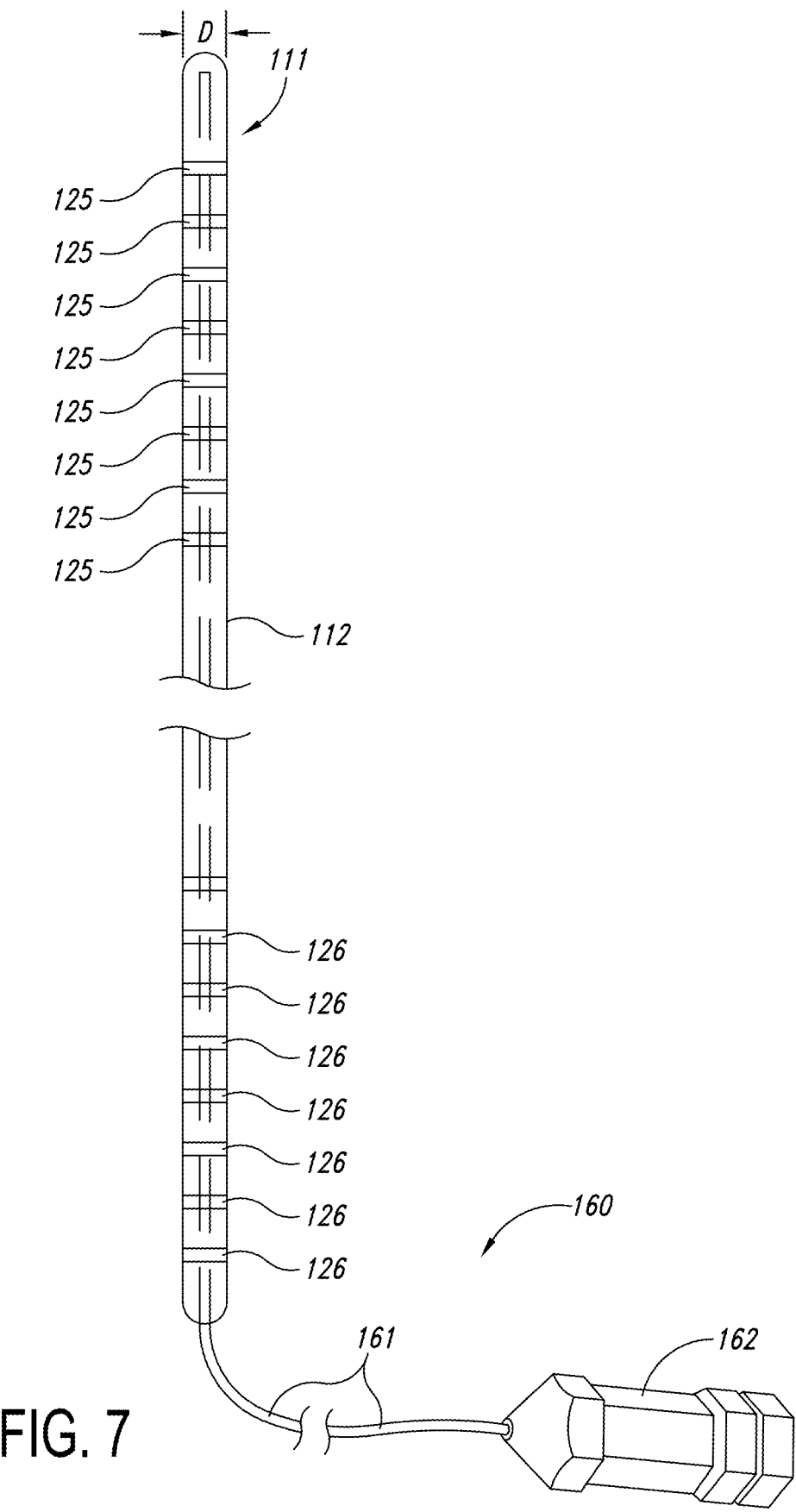
FIG. 7 is a partially schematic illustration of a signal delivery device having stimulation contacts and connector contacts, suitable for providing stimulation in accordance with embodiments of the present technology.

FIG. 7 is a partially schematic illustration of a representative signal delivery device 111 that includes an elongated lead body 112 having a circular or elliptical cross-section. The lead body 112 includes multiple electrodes or stimulation contacts 125 toward the distal end, and multiple connection contacts 126 toward the proximal end. In a particular embodiment, each multiple electrode or stimulation contact 125 is connected to a unique connection contact 126, to allow for delivery of stimulation to any single contact independently of all others. During the trial period (discussed above), the connection contacts 126 extend outside the patient's body and are coupled to an external stimulator. After the trial period is complete, the connection contacts 126 are connected to the implanted pulse generator 121 (FIG. 1). During implantation, a stylet 160 or other delivery device is temporarily inserted into the signal delivery device 111 to support it as it is positioned within the patient. Accordingly, the stylet 160 can include a shaft 161 and a handle 162. The shaft 161 is generally flexible, but more rigid than the signal delivery device 111, to allow the practitioner to insert the signal delivery device 111 and control its position during implantation. The signal delivery device can be introduced into the patient via a needle, and, once implanted, can be anchored in place. Suitable anchors can be attached to adjacent ligaments, bone, and/or other structures. In particular embodiments, the signal delivery device 111 can include tines and/or other features to resist unintended movements.

The lead body 112 can have a smaller diameter than that of leads typically used for dorsal stimulation. In particular, the diameter D of the lead body 112 can be less than one millimeter to account for the reduced space within the vertebral foramen 188 at ventral locations, when compared to dorsal locations.

The lead body 112 can carry eight stimulation contacts 125 and corresponding connection contacts 126 in a particular embodiment, illustrated in FIG. 7. In other embodiments, the lead body 112 can carry from four to 32 stimulation contacts 125 and corresponding connection contacts 126. The stimulation contacts 125 can have a length of from about one millimeter to about six millimeters, and in particular embodiments, about three millimeters. The edge-to-edge spacing between neighboring stimulation contacts 125 can range from one millimeter to 16 millimeters, and in a particular embodiment, is five millimeters. The contacts 125, 126 can be made from any suitable biocompatible, electrically and mechanically durable material, for example, a platinum-iridium alloy. The lead body 112 can be formed from any suitable biocompatible insulating material, for example, polyurethane.

In other embodiments, the signal delivery device 111 can have other configurations. For example, the signal delivery device 111 can have a paddle-type configuration, with an oval or flat cross-sectional shape, and with electrodes positioned on only one side (e.g., the flatter side) rather than encircling the lead body 112. Such a configuration can have particular utility outside the epidural space, where the flatter, paddle-type shape can be more readily stabilized outside the confines of the vertebral foramen 188 (FIG. 2). In such embodiments, the paddle lead can be sutured to a suitable structure, for example nearby fascia or bone.

7.0 Experimental Data

Figure 8A:
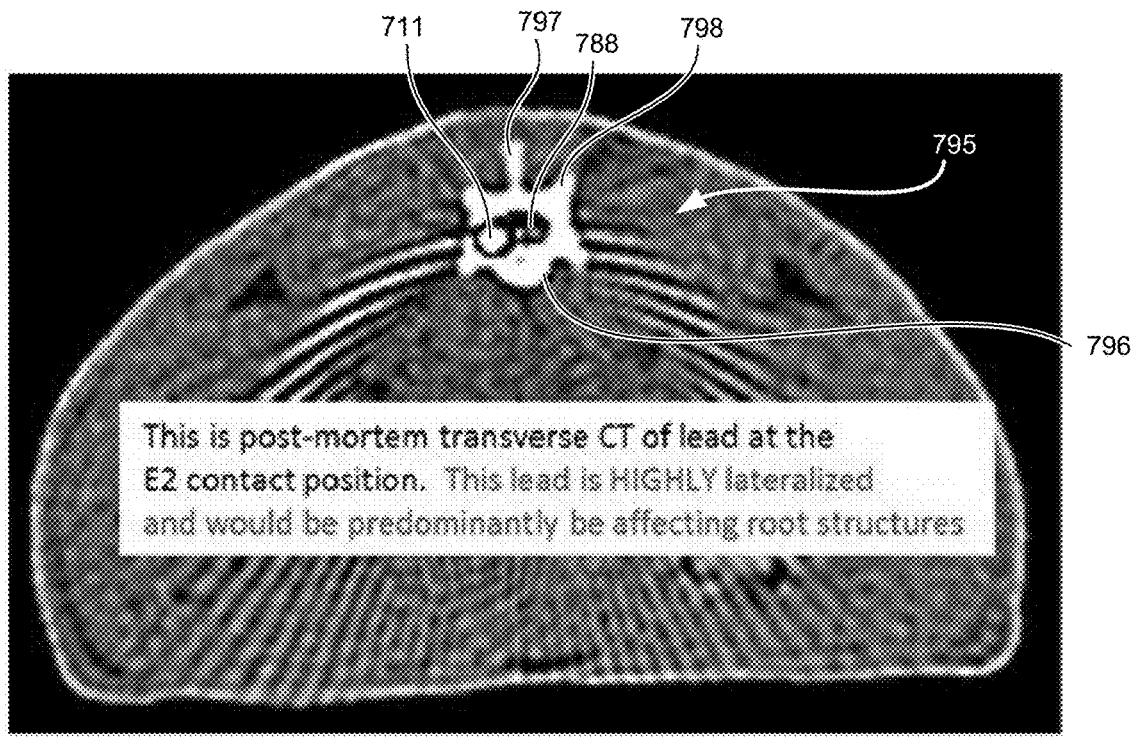
FIG. 8A is a CT scan taken at a cross-section of a rat's spinal cord, illustrating a signal delivery device positioned ventrally and laterally in accordance with an embodiment of the present technology.

FIG. 8A is a post-mortem, transverse CT scan of a signal delivery device 711 positioned in the epidural space of a rat spinal column. FIG. 8A illustrates the ventral body 796, spinous process 797, and transverse process 798 of the rat vertebra 795. The vertebra 795 encloses a vertebral foramen 788 in which the signal delivery device 711 is positioned. As shown in FIG. 8A, the signal delivery device 711 is not centered at the midline of the spinal cord, but is instead positioned far laterally in the vertebral foramen 788. In addition, the signal delivery device 711 is positioned ventrolaterally rather than dorsally within the foramen 788. Accordingly, it is expected to preferentially (e.g., predominantly) affect lateral neural structures, e.g., root fibers, both dorsal and ventral.

Figure 8B:
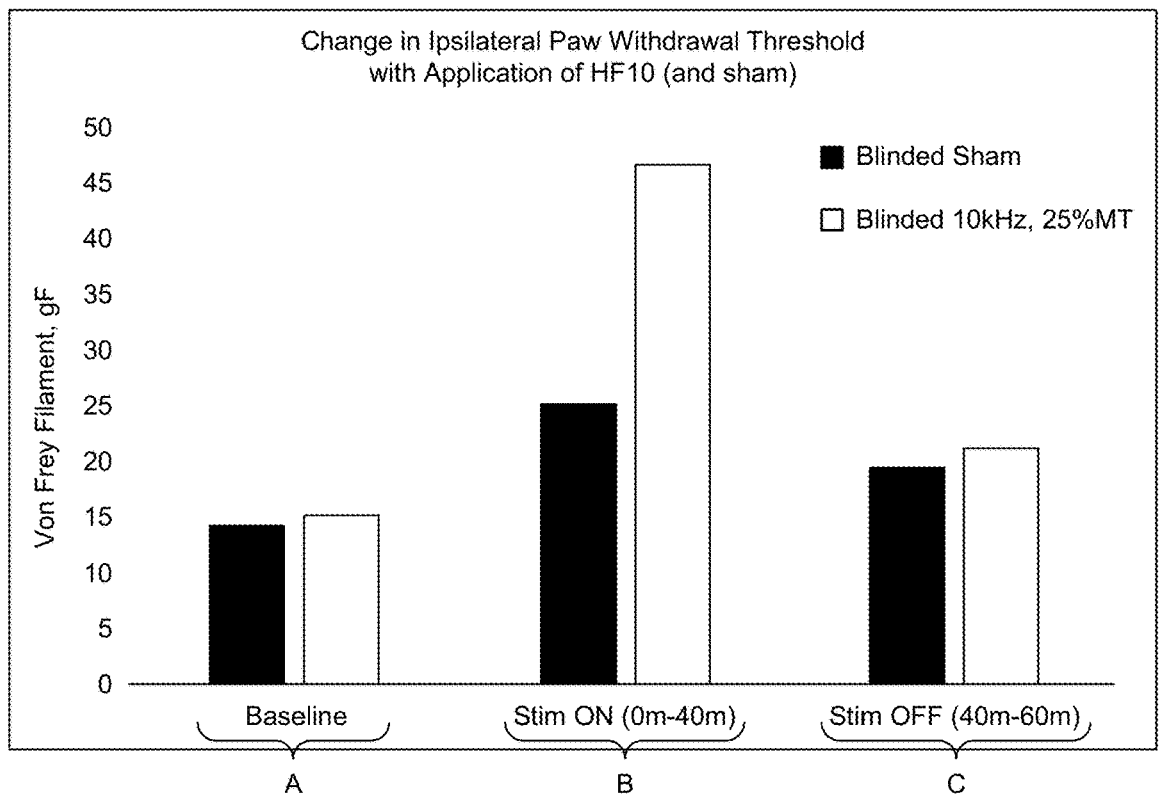
FIG. 8B graphically illustrates a comparison of animal test results obtained from (a) inhibitory stimulation provided by the signal delivery device shown in FIG. 8A, in accordance with an embodiment of the present technology, and (b) a sham stimulation.

FIG. 8B is a graph illustrating results obtained by stimulating a population of rats having a lead implanted as shown in FIG. 8A, with a 10 kHz signal at an amplitude of 25% of the rat's motor threshold. The data are compared with sham data, and the study was conducted in a blinded manner. FIG.

8B illustrates a comparison between the therapeutic signal and a sham signal at: baseline (A); then with the stimulation signal on (B); and then with the stimulation off (C). The vertical scale of FIG. 8B is the mechanical force applied to the rat's paw at the point the rat withdraws it. Accordingly, a higher force value on the y-axis corresponds to an increased tolerance of pain. As is shown in FIG. 8B, rats receiving the therapy had a significantly increased pain tolerance than rats that did not.

The results discussed above with reference to FIGS. 8A and 8B use pain reduction as an indication of efficacy. In traditional spinal cord stimulation, pain relief is believed to occur via the Gate Control Theory, which stipulates that activation of large diameter, innocuous sensory fibers will reduce the sensation of pain, typically carried by small-diameter dorsal root fibers. In traditional SCS, activation of these large diameter innocuous sensory fibers, located in the dorsal roots or dorsal columns, generates a paresthesia sensation in patients. Typically, the paresthesia-generating intensity ranges from 50% to 75% of the motor threshold. In this experiment, however, the delivered current pulses were far below this 'paresthesia threshold,' suggesting that the large diameter dorsal root were not activated. However, because pain signals are transmitted along small diameter fibers, it is expected that the selectivity of the signals for small diameter fibers can be applied to the sympathetic nervous system as well. Accordingly, it is expected that signals having the signal delivery characteristics described above can be applied to small diameter, unmyelinated or lightly myelinated sympathetic system fibers to produce corresponding effective therapeutic results (e.g., an inhibitory effect on an over-active sympathetic system) without unintended side effects (e.g., unwanted sensations and/or motor activity).

8.0 Representative Methods

Figure 9:
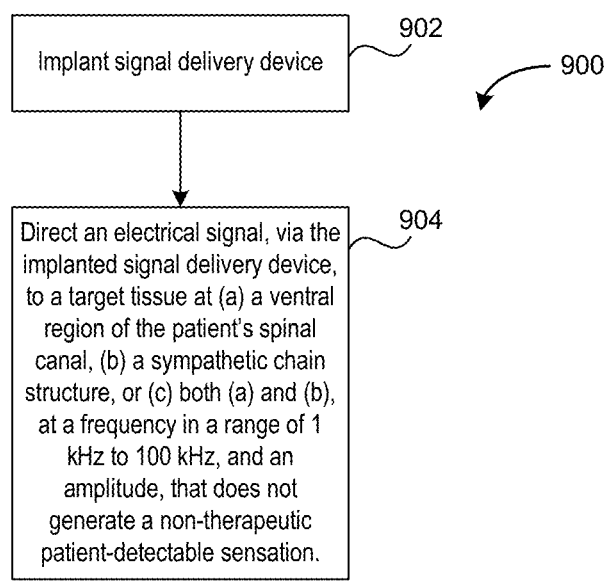
FIG. 9 is a flow diagram illustrating a representative method in accordance with an embodiment of the present technology.

FIG. 9 is a flow diagram of a method 900 for treating a patient in accordance with an embodiment of the present technology. Process portion 902 includes implanting a signal delivery device. As discussed above, the signal delivery device can include an elongated lead, a paddle, and/or another suitable device that carries electrodes, contacts, and/or other structures suitable for delivering an electrical signal to a target neural tissue. The signal delivery device can be implanted epidurally (e.g., at a ventral location) or extradurally (e.g., extravertebrally at or proximate to the patient's sympathetic chain).

Process portion 904 includes directing an electrical signal, via the implanted signal delivery device, to a target tissue (e.g., neuron, glial cell, and/or other tissue). The target tissue can be located ventrally at the patient's spinal cord region, for example, at the spinal cord itself or at the ventral roots. In other embodiments, an electrical signal is directed to the sympathetic chain structure in addition to or in lieu of being directed to the ventral region. For example, as discussed above, the electrical signal can be directed to the sympathetic trunk, sympathetic trunk ganglia, ventral ramus (of the spinal cord and/or a spinal nerve), gray ramus communicantes, and/or white ramus communicantes. The signal can be applied at a frequency in a range from 1 kHz to 100 kHz (or frequency sub-ranges noted above), and at an amplitude that does not generate an objectionable patient-detectable sensation and/or motor activity. Such objectionable patient-detectable sensations and/or motor activities may range from merely objectionable to intolerable. Objectionable sensations and/or motor activities may be non-therapeutic in some instances, and may be therapeutic (though still objectionable) in others. Accordingly, the signal may generate a therapeutic neural response that creates a patient-detectable sensation. For example, if the signal has the effect of increasing blood flow, the patient may feel warmer. However, in particular embodiments described above, the signal does not generate a sensation that is objectionable. Whether or not a sensation is objectionable can be readily determined, e.g., by assessing patient behavior and/or feedback. The amplitude of the signal can be selected based on general experience with similarly-situated patients, and/or on a patient-by-patient basis. For example, the practitioner can increase the amplitude of the signal (during a trial period) to identify the threshold at which the patient detects a sensation and/or experiences a motor response (e.g., twitching or jerking). Based on the threshold amplitude, the practitioner can set a lower amplitude for future therapeutic signal delivery. As discussed above, the signal amplitude is expected to be less than one milliamp at pulse widths less than 100 microseconds for most patients. Accordingly, the increment by which the practitioner increases/decreases the amplitude to identify the patient's threshold can be smaller than it is for typical SCS procedures, e.g., about 0.1 mA or less.

One feature of at least some of the embodiments described above is delivering an electrical therapy signal at a low amplitude (e.g., less than 0.5 mA) in a targeted manner to a neural population (or other target tissue) at a ventral region of the patient's spinal cord and/or at a sympathetic chain structure outside the spinal column. An expected advantage of this approach is that it can provide a therapeutic effect, e.g., controlling, inhibiting, and/or otherwise down-regulating an over-active sympathetic response. In addition, the low signal amplitude (alone and/or in combination with the targeted location to which it is directed) is expected to reduce or eliminate unintended effects. Such effects can include unwanted sensations and/or motor activity. This is unlike stimulation-created neural blocks, which typically require amplitudes above the activation threshold for the target neural population, and as a result, can generate uncomfortable sensory effects and/or undesirable motor effects as the signal amplitude is ramped up to an effective blocking value. It is expected that one reason the foregoing therapy may have the desired effect without creating collateral or ancillary effects is that the signal can selectively modulate small fibers, without also activating large fibers.

9.0 Additional Embodiments

Particular embodiments of the present technology are directed to methods for altering a patient's autonomic signaling. A representative method includes directing an electrical signal to a target tissue at one or both of a ventral region of the patient's spinal canal, or a sympathetic chain structure. The signal has a frequency in a range of 1 kHz to 100 kHz, and an amplitude that does not generate an objectionable, patient detectable sensory response. In further representative embodiments, the target tissue includes neurons or glial cells. The electrical signal can produce a change in at least one of the following autonomic functions: blood vessel diameter, blood pressure, cardiac function, kidney function, adrenal function, gastrointestinal function, autoimmune function, hepatic function, brain function, or pancreatic function.

In a further particular embodiment, a representative method includes at least reducing an activity of the patient's sympathetic nervous system by directing and inhibitory electrical signal to a target tissue located at at least one extravertebral cardiovascular ganglion, without the electrical signal generating a objectionable, patient-detectable sensory response. The electrical signal has a frequency in a range of 1 kHz to 10 kHz. In particular embodiments, the extravertebral cardiovascular ganglion can include a stellate sympathetic ganglion, a superior cervical ganglion, and inferior cervical ganglion, and/or an upper thoracic sympathetic ganglion. The inhibitory electrical signal can affect a cardiac parameter, including at least one of a cardiac rate, a cardiac conduction metric, or a blood pressure metric.

Still further embodiments are directed to systems for altering a patient's autonomic signaling. A representative system includes a signal generator programmed with instructions that, when executed, at least reduce an activity of the patient's sympathetic nervous system by generating a inhibitory electrical signal for delivery to a target tissue at (a) a ventral region of the patient's spinal canal, (b) a sympathetic chain structure, or (c) both (a) and (b). The signals are delivered at a frequency in the range of 1 kHz to 100 kHz, and at an amplitude that does not generate an objectionable, patient-detectable sensory response. The system further includes a signal delivery device coupled to the signal generator and having at least one electrode positionable at (a) the ventral region of the patient's spinal canal, (b) the sympathetic chain structure, or (c) both (a) and (b). In particular embodiments, a pulse width of the signal is from 1 μs to 1000 μs, e.g., from 10 μs to 30 μs. In another representative embodiment, the instructions, when executed, deliver the signal for at least 5 minutes continuously, at least 10 minutes continuously, or at least 30 minutes continuously. In still further embodiments, the signal is delivered continuously for 10 minutes, or up to 10 minutes.

Particular embodiments in which the electrical therapy signal is directed to an extravertebral target tissue (e.g., a sympathetic target) can operate differently than embodiments in which the signal is delivered to target tissue within the spinal canal. For example, extravertebral signals can be applied directly to efferent channels, without involving (or at least directly involving) spinal cord neural circuits.

Other embodiments of the present technology can vary from those specifically discussed above. For example, the signal delivery devices can have shapes and configurations other than those specifically shown and described above. In general, the signal delivery device will be implanted, but the source of energy applied to the signal delivery device may be external or internal. For example, in some embodiments, the energy source can include a battery in the IPG 121, as shown in FIG. 1. In other embodiments, an external power source can provide energy directly to the implanted signal delivery device via an RF link, and without an implanted battery or other energy storage device. Such an arrangement may be particularly suitable for patients who receive the therapy at a low duty cycle, and/or for patients who would prefer to wear a power source externally rather than have the power source implanted. The duty cycle can have patterns other than those specifically described above, e.g., one second of stimulation, followed by 20 seconds of no stimulation. In particular embodiments, it is expected that the beneficial inhibitory effect of the stimulation on the autonomic system may persist for a long period of time after the stimulation has ceased. For example, the patient may receive stimulation once a day for a relatively short period of time (e.g., ten minutes) to achieve a long-lasting effect. In such cases, the pulse generator need not include a rechargeable battery, and the patient can instead provide periodic power to the pulse generator via an inductive coil.

In any of the embodiments described herein, it is believed (without being bound by theory) that low intensity high frequency (e.g., 1 kHz-100 kHz) pulsatile electrical stimulation can create membrane hyperpolarization in post-synaptic neuronal cell bodies. This can be used to inhibit the spontaneous activity of these post-synaptic neurons as well as make them less responsive to incoming neural signals, as discussed above. Other mechanisms, in addition to or in lieu of hyperpolarization, can be responsible or responsible in part for the effects described above.

From the foregoing, it will be appreciated that specific embodiments of the disclosed technology have been described herein for purposes of illustration, but that various modifications may be made without deviating from the technology. Certain aspects of the technology described in the context of particular embodiments may be combined or eliminated in other embodiments. Further, while advantages associated with certain embodiments of the disclosed technology have been described in the context of those embodiments, other embodiments may also exhibit such advantages, and not all embodiments need necessarily exhibit such advantages to fall within the scope of the present technology. Accordingly, the present disclosure and associated technology can encompass other embodiments not expressly shown or described herein.

To the extent any materials incorporated by reference herein conflict with the present disclosure, the present disclosure controls.

I claim:

1. A method for altering a patient's autonomic signaling, comprising:
    based at least in part on a determination of an amplitude that does not generate an objectionable, patient-detectable sensory response, directing a first electrical signal to a target tissue at;
        (a) a ventral region of the patient's spinal canal,
        (b) a sympathetic chain structure, or
        (c) both (a) and (b);
    at (i) a frequency in a range of 1 kHz to 100 kHz and (ii) the determined amplitude; and
    modulating an inhibitory effect of the first electrical signal by applying to the patient a second electrical signal at;
        (a) the ventral region of the patient's spinal canal,
        (b) the sympathetic chain structure, or
        (c) both (a) and (b);
    at a frequency in a range of 10 Hz to under 1000 Hz.

2. The method of claim 1 wherein the target tissue at the ventral region includes a ventral root.

3. The method of claim 1 wherein the target tissue at the ventral region includes a ventral spinal cord structure.

4. The method of claim 1 wherein the target tissue includes neurons.

5. The method of claim 1 wherein the target tissue includes glial cells.

6. The method of claim 1 wherein the first electrical signal inhibits at least a portion of the patient's sympathetic division of the autonomic nervous system.

7. The method of claim 1 wherein the first electrical signal produces a change in at least one of the following autonomic functions: blood vessel diameter, blood pressure, cardiac function, kidney function, adrenal function, gastrointestinal function, autoimmune function, hepatic function, brain function or pancreatic function.

8. The method of claim 7 wherein the autonomic function is a cardiac function, and wherein the first electrical signal is directed to at least one stellate sympathetic ganglion.

9. The method of claim 7 wherein the autonomic function is a cardiac function, and wherein the first electrical signal affects at least one of heart rate or blood pressure.

10. The method of claim 7 wherein the autonomic function is a cardiac function, and wherein the first electrical signal addresses patient cardiac conduction metrics.

11. The method of claim 1 wherein directing the first electrical signal includes directing the first electrical signal without the first electrical signal generating a motor response in the patient.

12. The method of claim 1 wherein directing the first electrical signal includes directing the first electrical signal at an amplitude subthreshold to motor activation.

13. The method of claim 1 wherein directing the first electrical signal includes directing the first electrical signal at an amplitude subthreshold to objectionable sensory activation.

14. The method of claim 1 wherein the first electrical signal generates at least one action potential without generating the objectionable, patient-detectable sensory response.

15. The method of claim 1 wherein the amplitude is less than one mA.

16. The method of claim 1 wherein the target tissue includes an efferent neural population.

17. The method of claim 1 wherein a pulse width of the first electrical signal is from 1 microsecond to 1000 microseconds.

18. The method of claim 1 wherein a pulse width of the first electrical signal is from 10 microseconds to 30 microseconds.

19. The method of claim 1 wherein the first electrical signal is delivered for at least 30 minutes continuously.

20. The method of claim 1 wherein the first electrical signal is delivered for at least 5 minutes continuously.

21. The method of claim 1 wherein directing the first electrical signal includes directing the first electrical signal from an implanted pulse generator to an implanted signal delivery device.

22. The method of claim 1 wherein the first electrical signal is an inhibitory first electrical signal that at least reduces an activity level of the patient's sympathetic nervous system.

23. The method of claim 1 wherein the second electrical signal is applied to the target tissue.

24. The method of claim 1 wherein the target tissue is a first target tissue and includes a first target neural population, and wherein the second electrical signal is applied to a second target tissue including a second neural population different than the first target neural population.

25. The method of claim 1, further comprising directing the first electrical signal based at least in part on a feedback signal from the patient.

26. A system for altering a patient's autonomic signaling, comprising:
a signal generator programmed with instructions that, when executed and based at least in part on a determination of an amplitude that does not generate an objectionable, patient-detectable sensory response, at least reduce an activity level of the patient's sympathetic nervous system by generating an inhibitory first electrical signal for delivery to a target tissue at;
(a) a ventral region of the patient's spinal canal,
(b) a sympathetic chain structure, or
(c) both (a) and (b);
at (i) a frequency in a range of 1 kHz to 100 kHz and (ii) the determined amplitude, and generating a second electrical signal that modulates an inhibitory effect of the inhibitory first electrical signal for delivery to;
(a) the ventral region,
(b) the sympathetic chain structure, or
(c) both (a) and (b);
at a frequency in a range of 10 Hz to under 1000 Hz; and
a signal delivery device coupled to the signal generator and having at least one electrode positionable at;
(a) the ventral region of the patient's spinal canal,
(b) the sympathetic chain structure, or
(c) both (a) and (b).

27. The system of claim 26 wherein the amplitude is less than one mA.

28. The system of claim 26 wherein a pulse width of the first signal is from 1 microsecond to 1000 microseconds.

29. The system of claim 26 wherein a pulse width of the first signal is from 10 microseconds to 30 microseconds.

30. The system of claim 26 wherein the instructions, when executed, deliver the first signal for at least 30 minutes continuously.

31. The system of claim 26 wherein the instructions, when executed, deliver the first signal for at least 5 minutes continuously.

32. The system of claim 26 wherein the instructions, when executed, deliver the first signal for up to 10 minutes continuously.

33. The system of claim 26 wherein the signal generator is an implantable signal generator.

34. The system of claim 26 wherein the frequency has a value of 100 kHz.

35. The system of claim 26 wherein the second electrical signal is applied to the target tissue.

36. The system of claim 26 wherein the target tissue is a first target tissue and includes a first target neural population, and wherein the second electrical signal is for delivery to a second target tissue including a second neural population different than the first target neural population.

* * * * *

UNITED STATES PATENT AND TRADEMARK OFFICE
CERTIFICATE OF CORRECTION

PATENT NO. : 11,318,310 B1
APPLICATION NO. : 15/333763
DATED : May 3, 2022
INVENTOR(S) : Bradley It is certified that error appears in the above-identified patent and that said Letters Patent is hereby corrected as shown below:

On the Title Page

On the page 4, in Column 1, under "U.S. Patent Documents", Line 22, delete "Colbom" and insert -- Colborn --.

On the page 6, in Column 2, under "Other Publications", Line 24, delete "refactory" and insert -- refractory --.

On the page 6, in Column 2, under "Other Publications", Line 54, delete "Neurosco," and insert -- Neurosci, --.

On the page 6, in Column 2, under "Other Publications", Line 59, delete "BionicNAVIGATOR" and insert -- Bionic NAVIGATOR --.

On the page 7, in Column 1, under "Other Publications", Line 10, delete "Viennam" and insert -- Vienna --.

On the page 7, in Column 1, under "Other Publications", Line 15, delete "Suvival" and insert -- Survival --.

On the page 8, in Column 1, under "Other Publications", Line 20, delete "Refactory" and insert -- Refractory --.

On the page 9, in Column 1, under "Other Publications", Line 35, delete "Patienet" and insert -- Patient --.

On the page 9, in Column 1, Line 65, under "Other Publications", Line 19, delete "(Wulfsohn," and insert -- Wulfsohn, --.

Signed and Sealed this
Twelfth Day of September, 2023

Katherine Kelly Vidal
*Director of the United States Patent and Trademark Office*

CERTIFICATE OF CORRECTION (continued)
U.S. Pat. No. 11,318,310 B1

On the page 9, in Column 2, under "Other Publications", Line 34, delete "Anesthesiaand" and insert
-- Anesthesia and --.

On the page 10, in Column 2, under "Other Publications", Line 4, delete "Theshold" and insert
-- Threshold --.

On the page 10, in Column 2, under "Other Publications", Line 8, delete "Unabridge," and insert
-- Unabridged, --.

In the Specification

In Column 7, Lines 23-25, delete "http://humanphysiology.academy/Neurosciences %202015/Chapter %202/A.2.1%20Spinal %20Cord.htm." and insert
-- http://humanphysiology.academy/Neurosciences%202015/Chapter%202/A.2.1%20Spinal%20Cord.htm. --.